(12) United States Patent
Murphy et al.

(10) Patent No.: US 12,378,235 B2
(45) Date of Patent: Aug. 5, 2025

(54) HCK INHIBITORS FOR THE TREATMENT OF FIBROSIS AND CANCER

(71) Applicant: Icahn School of Medicine At Mount Sinai, New York, NY (US)

(72) Inventors: Barbara Murphy, New York, NY (US); Bhaskar Das, New York, NY (US); Chengguo Wei, New York, NY (US); Li Li, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 909 days.

(21) Appl. No.: 17/593,960

(22) PCT Filed: Apr. 1, 2020

(86) PCT No.: PCT/US2020/026093
§ 371 (c)(1),
(2) Date: Sep. 29, 2021

(87) PCT Pub. No.: WO2020/205921
PCT Pub. Date: Oct. 8, 2020

(65) Prior Publication Data
US 2022/0177464 A1    Jun. 9, 2022

Related U.S. Application Data

(60) Provisional application No. 62/828,143, filed on Apr. 2, 2019.

(51) Int. Cl.
| | | |
|---|---|---|
| *C07D 417/12* | (2006.01) | |
| *A61P 13/12* | (2006.01) | |
| *C07D 249/12* | (2006.01) | |
| *C07D 277/56* | (2006.01) | |
| *C07D 513/04* | (2006.01) | |
| *C07F 5/02* | (2006.01) | |

(52) U.S. Cl.
CPC ............ *C07D 417/12* (2013.01); *A61P 13/12* (2018.01); *C07D 249/12* (2013.01); *C07D 277/56* (2013.01); *C07D 513/04* (2013.01); *C07F 5/025* (2013.01)

(58) Field of Classification Search
CPC .............................. C07D 417/12; A61P 13/12
USPC ........................................................... 514/64
See application file for complete search history.

(56) References Cited

U.S. PATENT DOCUMENTS

2018/0118732 A1    5/2018   Lin et al.

OTHER PUBLICATIONS

Written Opinion and International Search Report in International Application No. PCT/US2020/026093, 11 pages. Jul. 24, 2020.
Pubchem, Substance Record for SID 319204107, retrieved on May 15, 2020 from https://pubchem.ncbi.nlm.nih.gov/substance/319204107, 6 pages. Nov. 29, 2016.
Pubchem, Substance Record for SID 79360011, retrieved on May 15, 2020 from https://pubchem.ncbi.nlm.nih.gov/substance/79360011, 7 pages. Jun. 12, 2009.
Pubchem, Substance Record for SID 47716945, retrieved on Jun. 29, 2020 from https://pubchem.ncbi.nlm.nih.gov/substance/47716945, 6 pages. Feb. 20, 2008.

*Primary Examiner* — Kahsay Habte
(74) *Attorney, Agent, or Firm* — Heslin Rothenberg Farley & Mesiti P.C.

(57) ABSTRACT

Compounds which are thiazole and triazole derivatives are disclosed, including compounds of the following genus:

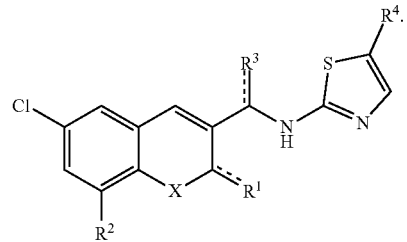

The compounds are inhibitors of hematopoietic cell kinase (HCK) and exhibit anti-fibrotic and anti-proliferative effects. They are useful in the treatment of a variety of disorders, including a fibrosis or a fibrotic disease, such as renal fibrosis.

20 Claims, 3 Drawing Sheets

HCK INHIBITORS FOR THE TREATMENT OF FIBROSIS AND CANCER

CROSS REFERENCE TO RELATED APPLICATIONS

This application is a U.S. National Phase filing under 35 U.S.C. § 371 of International Application PCT/US2020/026093, filed Apr. 1, 2020, and published as WO 2020/205921 on Oct. 8, 2020. International Application PCT/US2020/026093 claims priority from U.S. provisional application 62/828,143, filed Apr. 2, 2019. The entire disclosures of each of these prior applications are hereby incorporated herein by reference.

GOVERNMENT RIGHTS STATEMENT

This invention was made with government support under grant number AI070107 awarded by The National Institutes of Health. The government has certain rights in the invention.

BACKGROUND OF THE INVENTION

Technical Field

This invention relates to thiazole- or triazole-containing compounds that are inhibitors of HCK. The compounds disclosed are useful in treatment of fibrosis, fibrotic diseases, and various cancers and autoimmune diseases.

Background Information

Many people are affected unfavorably by fibrotic diseases, which can cause adverse life changes, organ failure, and death. Fibrotic disease is found in many organs of the body, yet its pathophysiology is not well understood. Cirrhosis (liver), keloids (skin), and pulmonary fibrosis and cystic fibrosis (lung) are diseases and disorders that affect many people worldwide. Fibrosis and fibrotic diseases can have genetic causes and/or may be induced by external factors, such as infection, surgery, diet, or radiation.

Renal fibrosis is a representative fibrotic disease, and it is an important topic that attracts broad interest in nephrology owing to its status as a hallmark and common outcome across all kinds of progressive chronic kidney disease (CKD). CKD and chronic renal allograft injury (CAI) are worldwide health problems. They are associated with high mortality and morbidity as well as tremendous costs associated with renal replacement. Renal fibrosis is the final common pathway of progression of CKD and CAI. Renal fibrosis underlies the progression of chronic kidney disease (CKD) to end-stage renal disease (ESRD). CKD affected approximately 38.56 million people in the United States in 2012, and it is estimated that the prevalence of CKD in the United States will increase to 46.23 million by 2022. According to the NIDDK, 14% of Americans were afflicted with CKD in 2012.

There is currently no cure for CKD, and current treatments are aimed at slowing its progression. For instance, renin-angiotensin-aldosterone system blockers may decrease the risk of progression, but only by about 20%. Dialysis and renal transplant are the only options for patients with ESRD. However, renal transplants bring a high risk of rejection or developing fibrosis, and dialysis is a high-cost treatment.

Hematopoietic cell kinase (HCK) is a member of the Src-family of non-receptor tyrosine kinases. Previous work has shown that hematopoietic cell kinase (HCK) is the key driver in renal fibrosis progression. HCK has been shown to be strongly associated with renal fibrosis in in vitro and in vivo experiments. Further, data have shown that targeting HCK can attenuate renal fibrosis and improve kidney functions. HCK also has recently been identified as a cancer target of the Src-Tyrosine Kinase family. Previous work has demonstrated that inhibition of HCK also improved renal function, reduced albuminuria, decreased collagen and fibronectin expression, and inhibited expression of profibrotic markers in animal models with lupus nephritis and folic acid nephropathy.

There is an urgent need for safe and effective anti-fibrotic treatments. The inhibition of HCK can provide a therapeutic strategy for the treatment of fibrosis and fibrotic diseases in patients.

SUMMARY OF THE INVENTION

In a first aspect the invention relates to compounds of formula (I):

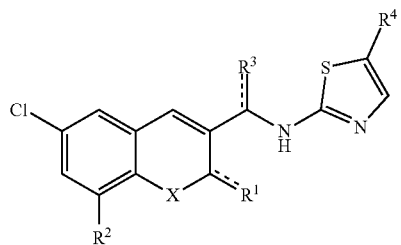

wherein
X is selected from O, $NR^6$, or S;
$R^1$ is selected from O or phenyl optionally substituted with one or more substituents selected from $C_1$-$C_6$ alkyl, $C_1$-$C_6$ alkoxy, $C_1$-$C_6$ fluoroalkyl and halogen;
$R^2$ is selected from halogen, hydrogen, $C_1$-$C_6$ alkyl, $C_1$-$C_3$ alkoxy, $C_1$-$C_3$ fluoroalkyl or phenyl;
$R^3$ is selected from O, —OH, or —CN;
$R^4$ is selected from —C(=O)$OR^5$, tetrazole, triazole, —CN, —C(=O)$NH_2$, —$BOR^7OR^8$, or —$BF_3^-$;
$R^5$ is selected from hydrogen or $C_1$-$C_6$ alkyl;
$R^6$ is selected from hydrogen or $C_1$-$C_6$ alkyl;
$R^7$ and $R^8$ are each independently selected from hydrogen or $C_1$-$C_6$ alkyl or, together with the boron and the oxygens to which they are attached, form a 5- or 6-membered ring optionally substituted with $C_1$-$C_6$ alkyl; and
------ independently in each instance indicates a single bond or a double bond.

In a second aspect, the invention relates to compounds of formula II:

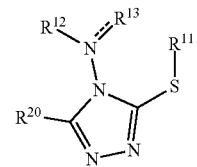

wherein

- ------ independently in each instance indicates a single bond or a double bond;
- $R^{11}$ hydrogen or $C_1$-$C_6$ alkyl;
- $R^{12}$ is hydrogen or $C_1$-$C_6$ alkyl or, when ------ is a double bond, is absent;
- $R^{13}$ is selected from hydrogen or —$CR^{14}R^{15}R^{16}$; or
- $R^{11}$ and $R^{13}$ form a 5- to 7-membered heterocyclic or heteroaryl ring, substituted with $R^{16}$;
- $R^{14}$ is hydrogen or, when ------ is a double bond, is absent;
- $R^{15}$ is selected from hydrogen, cyano, $C_1$-$C_6$ haloalkyl, —C(=O)O($C_1$-$C_6$ alkyl), or —C(=O)NH$_2$, or, when $R^{11}$ and $R^{13}$ form a ring, is absent;
- $R^{16}$ is a phenyl ring, optionally substituted with 1, 2, or 3 instances of $R^{17}$;
- $R^{17}$ is selected independently in each instance from halogen, $C_1$-$C_6$ alkyl, $C_1$-$C_6$ alkoxy, $C_1$-$C_6$ haloalkyl, $C_1$-$C_6$ haloalkoxy, —$BOR^{18}OR^{19}$, —$BF_3^-$, —CN, —C(=O)NH$_2$, —C(=O)$OR^{17a}$, tetrazole, triazole, or —NO$_2$;
- $R^{17a}$ is selected from hydrogen or $C_1$-$C_6$ alkyl;
- $R^{18}$ and $R^{19}$ are each independently selected from hydrogen or $C_1$-$C_6$ alkyl or, together with the boron and the oxygens to which they are attached, form a 5- or 6-membered ring optionally substituted with $C_1$-$C_6$ alkyl; and
- $R^{20}$ is selected from hydrogen, $C_1$-$C_6$ alkyl, a 5- or 6-membered heteroaryl optionally substituted with $C_1$-$C_6$ alkyl, or phenyl optionally substituted independently in each instance with one or more of halogen, $C_1$-$C_6$ alkyl, $C_1$-$C_3$ alkoxy, $C_1$-$C_3$ haloalkoxy, $C_1$-$C_3$ haloalkyl, a heterocycle, —CN, and —C(=O)NH$_2$.

In a third aspect, the invention relates to compounds of formula III:

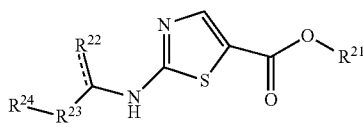

III wherein

- $R^{21}$ is hydrogen or $C_1$-$C_6$ alkyl;
- ------ independently in each instance indicates a single bond or a double bond;
- $R^{22}$ is cyano when ------ is a single bond, or is selected from =O or =N—OH when ------ is a double bond;
- $R^{23}$ is absent or is selected from —CH=CH— or a 5- or 6-membered heteroaryl;
- $R^{24}$ is a phenyl ring, optionally substituted with 1, 2, or 3 instances of $R^{25}$; and
- $R^{25}$ is selected independently in each instance from halogen, $C_1$-$C_6$ alkyl, $C_1$-$C_6$ alkoxy, $C_1$-$C_6$ haloalkyl, $C_1$-$C_6$ haloalkoxy, —$BOR^{26}OR^{27}$, —$BF_3^-$, —CN, —C(=O)NH$_2$, —C(=O)$OR^{27a}$, tetrazole, triazole, —NO$_2$, guanidine, and an amidoxime.
- $R^{26}$ and $R^{27}$ are each selected from hydrogen or $C_1$-$C_6$ alkyl or, together with the boron and the oxygens to which they are attached, form a 5- or 6-membered ring optionally substituted with one or more $C_1$-$C_6$ alkyl groups; and $R^{27a}$ is selected from hydrogen or $C_1$-$C_6$ alkyl.

In a fourth aspect, the invention relates pharmaceutical compositions comprising the compounds described herein.

In a fifth aspect, the invention relates to methods and uses of compounds or pharmaceutical compositions described herein for the treatment of a disease chosen from fibrosis or a fibrotic disease.

In a sixth aspect, the invention relates to methods and uses of compounds or pharmaceutical compositions described herein for the treatment of a disease chosen from chronic kidney disease, renal fibrosis, or chronic renal allograft injury in a patient.

In a seventh aspect, the invention relates to methods and uses of compounds or pharmaceutical compositions described herein for the treatment of a disease chosen from solid malignancy or a hematological malignancy, such as a leukemia or a lymphoma.

In an eighth aspect, the invention relates to methods and uses of compounds or pharmaceutical compositions described herein for the treatment of an autoimmune or inflammatory disease.

In a ninth aspect, the invention relates to methods and uses of compounds or pharmaceutical compositions described herein for treating a disease or disorder in a patient where the disease or disorder involves the dysregulation of hematopoietic cell kinase (HCK) signaling.

In a tenth aspect, the invention relates to methods and uses of compounds or pharmaceutical compositions described herein for inhibiting hematopoietic cell kinase (HCK) activation.

These, and other objects, features and advantages of this invention will become apparent from the following detailed description of the various aspects of the invention taken in conjunction with the accompanying drawings.

DETAILED DESCRIPTION OF THE INVENTION

Figure 1:
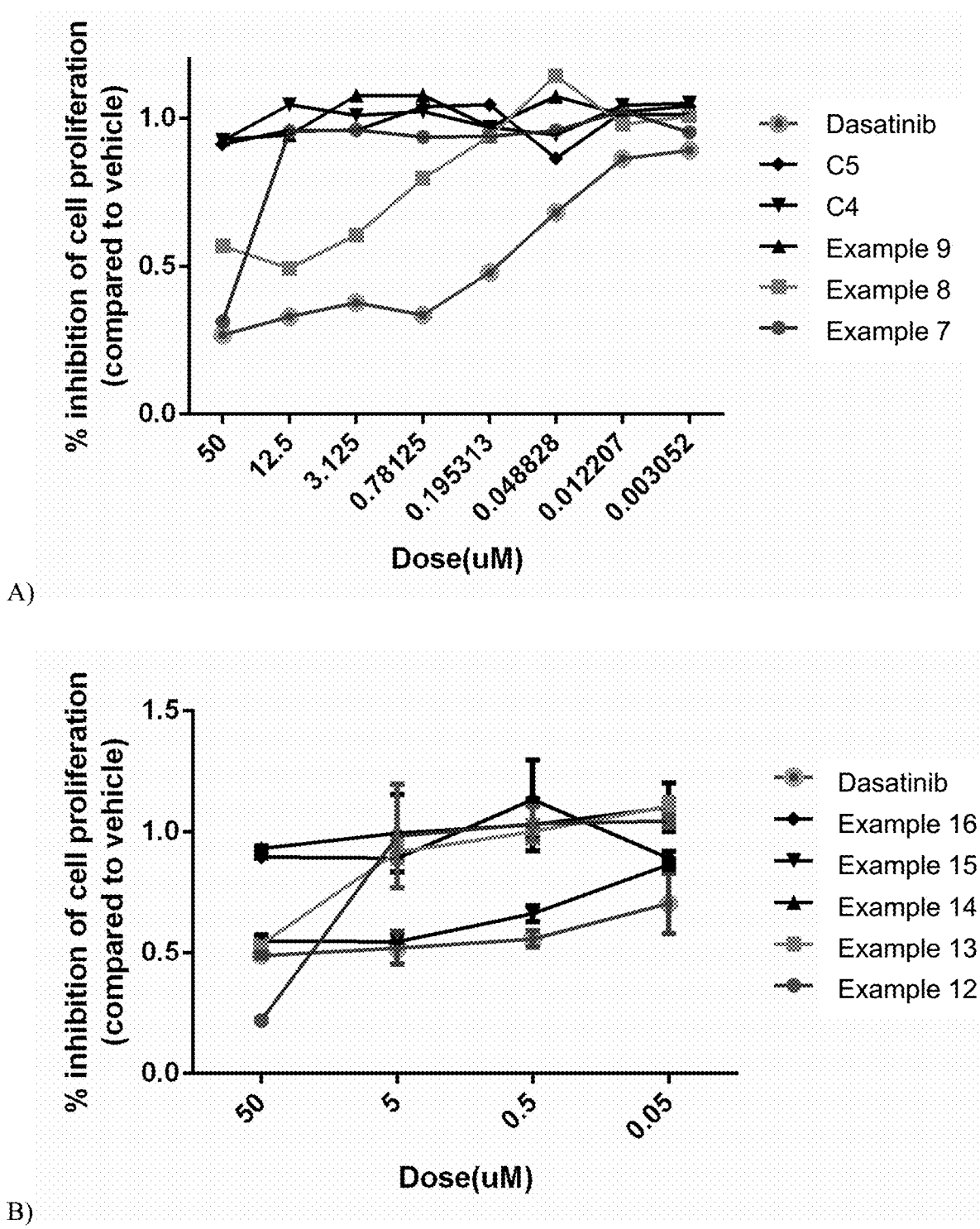
FIG. 1 depicts the inhibition of cell proliferation after treatment with compounds of the invention in different doses.

Renal fibrosis is an important treatment target for many pathophysiologically distinct diseases, since a large variety of diseases converge finally into this single process. However, effective therapies do not exist for renal fibrosis or fibrotic diseases of other organs. It has been shown that targeting HCK can attenuate renal fibrosis and improve kidney functions.

HCK is also thought to be a promising therapeutic target for the treatment of cancer, both solid tumors and hematological malignancies. A relationship between HCK and some viral proteins, such as those related to Human Immunodeficiency Virus (HIV) infection (and AIDS), has also been shown.

HCK is expressed in cells of the myeloid and B-lymphocyte cell lineages. Various types of cancer, including leukemia and solid tumors, are associated with the overactivation of HCK expression. Overactivation of HCK has also been found to have a detrimental effect on drug efficacy and patient survival rates.

Elevated HCK expression in cells is associated with autoimmune and inflammatory diseases. Rheumatoid arthritis (RA) is an autoimmune disease, and one of the hallmarks of RA is inflammation in the individual's joints. HCK was shown to be expressed selectively in fibroblast-like synoviocytes, which are mediators of inflammation in patients with RA. Similarly, the neutrophils of COPD patients have significantly elevated HCK protein levels. Inhibition of HCK in these diseases provides a promising therapy for treating these diseases.

Compounds have been found that are small molecule inhibitors of HCK, with high binding affinity and fewer side effects to attenuate kidney fibrosis. These compounds show potent and specific cytotoxicity in HCK-expressing cells, thereby indicating significant potential for the treatment of patients suffering from a variety of diseases and disorders. In previous studies, HCK was found to be a key mediator of renal fibrosis through the TGF-β/Smad3 pathway.

Substituents are generally defined when introduced and retain that definition throughout the specification and in all independent claims.

In a composition aspect, the invention relates to compounds of formula I:

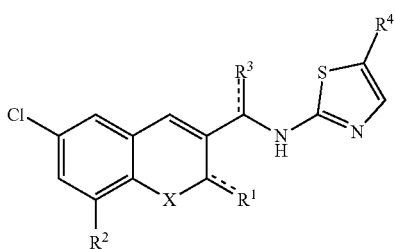

as described above.

In some embodiments, X is O. In some embodiments, X is $NR^6$. In some embodiments, X is S.

In some embodiments, $R^6$ is hydrogen. In other embodiments, $R^6$ is $C_1$-$C_6$ alkyl. In some embodiments, $R^6$ is selected from methyl, ethyl, propyl or isopropyl. In some embodiments, $R^6$ is methyl. In some embodiments, $R^6$ is selected from hydrogen or methyl.

In some embodiments, $R^1$ is unsubstituted phenyl and ------ is a single bond. In other embodiments, $R^1$ is phenyl substituted with one or more substituents selected from $C_1$-$C_6$ alkyl, $C_1$-$C_6$ alkoxy, $C_1$-$C_6$ fluoroalkyl and halogen. In still other embodiments, $R^1$ is O and ------ is a double bond.

The person of skill will understand that when ------ represents a double bond, the carbon to which it is attached will possess a proton that is not present when ------ represents a single bond. This proton is not drawn in the formulae depicted herein.

In some embodiments, $R^2$ is halogen. In other embodiments, $R^2$ is chloro. In some embodiments, $R^2$ is fluoro. In some embodiments, $R^2$ is hydrogen. In still other embodiments, $R^2$ is $C_1$-$C_3$ alkyl. In yet other embodiments, $R^2$ is $C_1$-$C_3$ alkoxy. In other embodiments, $R^2$ is $C_1$-$C_3$ fluoroalkyl. In some embodiments, $R^2$ is methyl. In some embodiments, $R^2$ is methoxy. In yet other embodiments, $R^2$ is unsubstituted phenyl.

In some embodiments, $R^3$ is O and ------ is a double bond. In other embodiments, $R^3$ is —OH and ------ is a single bond. In some embodiments, $R^3$ is —CN and ------ is a single bond.

In some embodiments, $R^4$ is —C(=O)$OR^5$. In other embodiments, $R^4$ is tetrazole. In still other embodiments, $R^4$ is triazole. In some embodiments, $R^4$ is —$CN^-$. In yet other embodiments, $R^4$ is —C(=O)$NH_2$. In further embodiments, $R^4$ is —$BOR^7OR^8$. In some embodiments, $R^4$ is —$BF_3^-$.

In some embodiments, $R^5$ is hydrogen. In other embodiments, $R^5$ is $C_1$-$C_6$ alkyl. In some embodiments, $R^5$ is methyl. In some embodiments, $R^5$ is ethyl. In some embodiments, $R^5$ is i-propyl. In some embodiments, $R^5$ is n-propyl.

In some embodiments, $R^7$ and $R^8$ are each independently selected from hydrogen or $C_1$-$C_6$ alkyl. In other embodiments, $R^7$ and $R^8$, together with the boron and the oxygens to which they are attached, form a 5- or 6-membered ring. In some of these embodiments, the 5- or 6-membered ring is substituted with one or more $C_1$-$C_6$ alkyl groups. In still other embodiments, the 5- or 6-membered ring is substituted with one or more methyl groups. In other embodiments, $R^7$ and $R^8$, together with the boron and the oxygens to which they are attached, form a 5-membered ring. In some of these embodiments, $R^7$ and $R^8$, together with the boron and the oxygens to which they are attached, form a 5-membered ring substituted with one or more $C_1$-$C_6$ alkyl groups, and in some embodiments, the $C_1$-$C_6$ alkyl groups are methyl groups. In some embodiments, $R^7$ and $R^8$, together with the boron and the oxygens to which they are attached, form

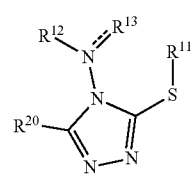

In some embodiments:
X is O or NH;
$R^1$ is selected from optionally substituted phenyl or O;
$R^2$ is selected from halogen or chloro;
$R^3$ is selected from O or CN;
$R^4$ is —C(=O)$OR^5$;
$R^5$ is ethyl; and
------ independently in each instance indicates a single bond or a double bond.

In a composition aspect, the invention relates to compounds of formula II:

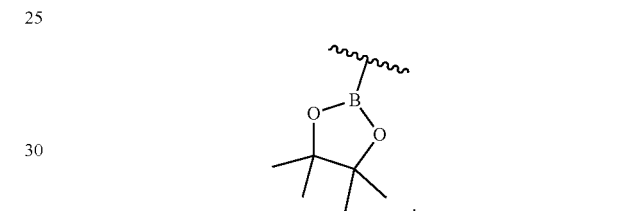

as described above.

In some embodiments, $R^{12}$ is hydrogen. In other embodiments, $R^{12}$ is $C_1$-$C_6$ alkyl. In still other embodiments, $R^{12}$ is selected from methyl, ethyl, propyl or isopropyl. In some embodiments, $R^{12}$ is methyl. In some embodiments, ------ is a double bond and $R^{12}$ is absent.

In some embodiments, $R^{11}$ is hydrogen. In other embodiments, $R^{11}$ is $C_1$-$C_6$ alkyl. In still other embodiments, $R^{11}$ is selected from methyl, ethyl, propyl or isopropyl. In some embodiments, $R^{11}$ is methyl.

In some embodiments, $R^{11}$ and $R^{13}$ form a 5- to 7-membered heterocyclic ring substituted with $R^{16}$. In some embodiments, $R^{11}$ and $R^{13}$ form a 5- to 7-membered heteroaryl ring substituted with $R^{16}$. In some embodiments, $R^{11}$ and $R^{13}$ form a compound of formula:

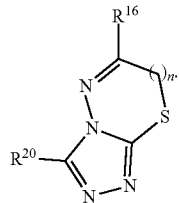

In some embodiments, n is 0. In other embodiments, n is 1. In still other embodiments, n is 2.

In some embodiments, the compound is of formula:

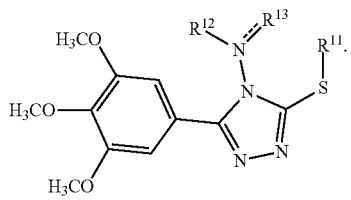

In some embodiments, $R^{13}$ is hydrogen. In other embodiments, $R^{13}$ is $-CR^{14}R^{15}R^{16}$.

In some embodiments, ------ is a single bond. In other embodiments, ------ is a double bond.

In some embodiments, ------ is a single bond and $R^{14}$ is hydrogen. In other embodiments, ------ is a double bond and $R^{14}$ is absent.

In some embodiments, $R^{15}$ is hydrogen. In other embodiments, $R^{15}$ is cyano. In still other embodiments, $R^{15}$ is $C_1$-$C_6$ haloalkyl. In further embodiments, $R^{15}$ is $-CF_3$. In other embodiments, $R^{15}$ is $-C(=O)O(C_1$-$C_6$ alkyl). In some embodiments, $R^{15}$ is $-C(=O)OCH_3$. In other embodiments, $R^{15}$ is $-C(=O)NH_2$. In still other embodiments, when $R^{11}$ and $R^{13}$ form a ring, $R^{15}$ is absent. In other embodiments, ------ is a double bond and $R^{15}$ is hydrogen.

In some embodiments, $R^{16}$ is an unsubstituted phenyl ring. In other embodiments, $R^{16}$ is a phenyl ring substituted with 1 instance of $R^{17}$. In yet other embodiments, $R^{16}$ is a phenyl ring substituted with 2 instances of $R^{17}$. In other embodiments, $R^{16}$ is a phenyl ring substituted with 3 instances of $R^{17}$. In some embodiments, one instance of $R^{17}$ is in the para position. In further embodiments, $R^{16}$ is a phenyl ring substituted with 1 instance of $R^{17}$ in the para position. Each instance of $R^{17}$ is selected independently. As non-limiting illustrative examples, there may be one instance of $R^{17}$ that is fluoro; or there may be two instances of $R^{17}$, both of which are chloro; or there may be three instances of $R^{17}$, one of which is chloro, and two of which are methyl.

In some embodiments, $R^{17}$ is hydrogen. In other embodiments, $R^{17}$ is halogen. In still other embodiments, $R^{17}$ is chloro. In yet other embodiments, $R^{17}$ is fluoro. In further embodiments, $R^{17}$ is bromo. In still other embodiments, $R^{17}$ is $C_1$-$C_6$ alkyl. In yet other embodiments, $R^{17}$ is methyl. In some embodiments, $R^{17}$ is $C_1$-$C_6$ alkoxy. In other embodiments, $R^{17}$ is methoxy. In further embodiments, $R^{17}$ is $C_1$-$C_6$ haloalkyl. In other embodiments, $R^{17}$ is $-CF_3$. In some embodiments, $R^{17}$ is $C_1$-$C_6$ haloalkoxy. In other embodiments, $R^{17}$ is $-OCF_3$. In still other embodiments, $R^{17}$ is $-BF_3$. In some embodiments, $R^{17}$ is $-BOR^{18}OR^{19}$. In other embodiments, $R^{17}$ is

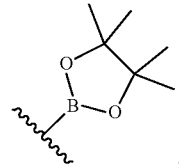

In further embodiments, $R^{17}$ is $-CN$. In some embodiments, $R^{17}$ is $-C(=O)NH_2$. In other embodiments, $R^{17}$ is tetrazole. In still other embodiments, $R^{17}$ is triazole. In some embodiments, $R^{17}$ is $-NO_2$. In some embodiments, $R^{17}$ is $-C(=O)OR^{17a}$.

In some embodiments, $R^{17a}$ is hydrogen. In other embodiments, $R^{17a}$ is $C_1$-$C_6$ alkyl. In still other embodiments, $R^{17a}$ is methyl.

In some embodiments, $R^{18}$ is hydrogen. In other embodiments, $R^{18}$ is $C_1$-$C_6$ alkyl. In still other embodiments, $R^{18}$ is methyl.

In some embodiments, $R^{19}$ is hydrogen. In other embodiments, $R^{19}$ is $C_1$-$C_6$ alkyl. In still other embodiments, $R^{19}$ is methyl.

In other embodiments, $R^{18}$ and $R^{19}$, together with the boron and the oxygens to which they are attached, form a 5-membered ring. In some of these embodiments, $R^{18}$ and $R^{19}$, together with the boron and the oxygens to which they are attached, form a 5-membered ring substituted with one or more $C_1$-$C_6$ alkyl groups, and in some embodiments, the $C_1$-$C_6$ alkyl groups are methyl groups. In some embodiments, $R^{18}$ and $R^{19}$, together with the boron and the oxygens to which they are attached, form

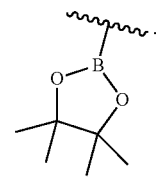

In some embodiments, $R^{20}$ is hydrogen. In other embodiments, $R^{20}$ is $C_1$-$C_6$ alkyl. In still other embodiments, $R^{20}$ is methyl. In further embodiments, $R^{20}$ is a 5- or 6-membered heteroaryl, optionally substituted with $C_1$-$C_6$ alkyl. In some embodiments, $R^{20}$ is phenyl, optionally substituted independently in each instance with one or more substituents selected from halogen, $C_1$-$C_6$ alkyl, $C_1$-$C_3$ alkoxy, $C_1$-$C_3$ haloalkoxy, $C_1$-$C_3$ haloalkyl, a heterocycle, $-CN$, and $-C(=O)NH_2$.

In a composition aspect, the invention relates to compounds of formula III:

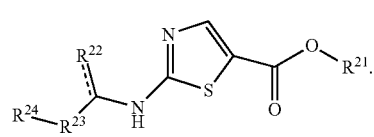

as described above.

In some embodiments, $R^{23}$ is absent, and the compound is of formula:

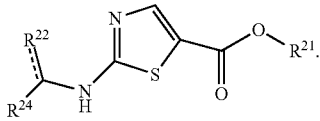

In other embodiments, $R^{23}$ is —CH=CH—, and the compound is of formula:

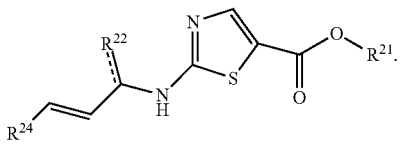

In still other embodiments, $R^{23}$ is a 5- or 6-membered heteroaryl. In some embodiments, $R^{23}$ is selected from isoxazole, oxazole, furan, and triazole. In other embodiments, $R^{23}$ is selected from isoxazole and oxazole. In further embodiments, $R^{23}$ is isoxazole. In some embodiments, $R^{23}$ is isoxazole and the compound is of formula:

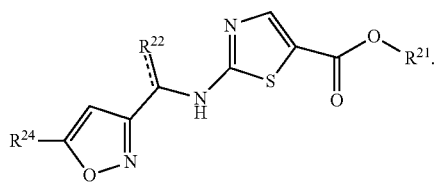

In some embodiments, $R^{21}$ is hydrogen. In some embodiments, $R^{21}$ is $C_1$-$C_6$ alkyl. In other embodiments, $R^{21}$ is methyl. In still other embodiments, $R^{21}$ is ethyl.

In some embodiments, ====== is a double bond and $R^{22}$ is O, forming=O. In other embodiments, ====== is a single bond and $R^{22}$ is cyano, forming —CN. In still other embodiments, ====== is a double bond and $R^{22}$ is N—OH, forming=N—OH.

In some embodiments, $R^{24}$ is an unsubstituted phenyl ring. In other embodiments, $R^{24}$ is a phenyl ring substituted with 1 instance of $R^{25}$. In still other embodiments, $R^{24}$ is a phenyl ring substituted with 2 instances of $R^{25}$. In further embodiments, $R^{24}$ is a phenyl ring substituted with 3 instances of $R^{25}$. In some embodiments, $R^{24}$ is

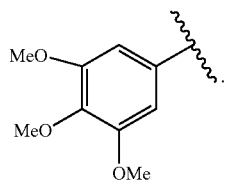 [SMILES: *c1cc(OC)c(OC)c(OC)c1]

In other embodiments, $R^{24}$ is

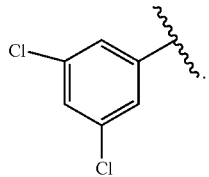 [SMILES: *c1cc(Cl)cc(Cl)c1]

In some embodiments, $R^{25}$ is selected independently in each instance from halogen, $C_1$-$C_6$ alkyl, $C_1$-$C_6$ alkoxy, $C_1$-$C_6$ haloalkyl, $C_1$-$C_6$ haloalkoxy, —BOR$^{26}$OR$^{27}$, —BF$_3^-$, —CN, —C(=O)NH$_2$, —C(=O)OR$^{27a}$, tetrazole, triazole, —NO$_2$, guanidine, and an amidoxime. In some embodiments, $R^{25}$ is selected independently in each instance from chloro, fluoro, methoxy, —OCF$_3$, —B(OH)$_2$ or

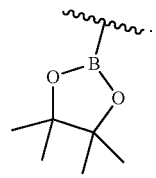

In other embodiments, one instance of $R^{25}$ is in the para position. In still other embodiments, $R^{25}$ is —B(OH)$_2$ in the para position. In further embodiments, $R^{25}$ is

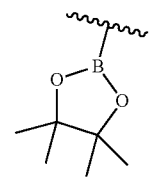

in the para position. Each instance of $R^{25}$ is selected independently. As non-limiting illustrative examples, there may be one instance of $R^{25}$ that is fluoro; or there may be two instances of $R^{25}$, both of which are chloro; or there may be three instances of $R^{25}$, one of which is chloro, and two of which are methyl, or all three of which are methoxy.

In some embodiments, each of $R^{26}$ and $R^{27}$ is selected from hydrogen or $C_1$-$C_6$ alkyl, and in some cases methyl. In other embodiments, $R^{26}$ and $R^{27}$, together with the boron and the oxygens to which they are attached, form a 5- or 6-membered ring. In some of these embodiments, the 5- or 6-membered ring is substituted with one or more $C_1$-$C_6$ alkyl groups. In still other embodiments, the 5- or 6-membered ring is substituted with one or more methyl groups. In other embodiments, $R^{26}$ and $R^{27}$, together with the boron and the oxygens to which they are attached, form a 5-membered ring. In some of these embodiments, $R^{26}$ and $R^{27}$, together with the boron and the oxygens to which they are attached, form a 5-membered ring substituted with one or more $C_1$-$C_6$ alkyl groups, and in some embodiments, the $C_1$-$C_6$ alkyl groups are methyl groups. In some embodiments, $R^{26}$ and $R^{27}$, together with the boron and the oxygens to which they are attached, form

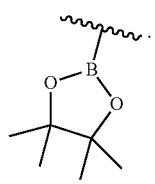

In some embodiments, $R^{27a}$ is hydrogen. In other embodiments, $R^{27a}$ is $C_1$-$C_6$ alkyl. In some embodiments, $R^{27a}$ is methyl.

The compounds described herein contain three or more asymmetric centers and may thus give rise to enantiomers, diastereomers, and other stereoisomeric forms which may be defined in terms of absolute stereochemistry as (R)- or (S)-. The present invention is meant to include all such possible diastereomers as well as their racemic and optically pure forms. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of indeterminate absolute configuration. For example, when $R^3$ is —OH or —CN (that is, connected by a single bond), the graphic representation

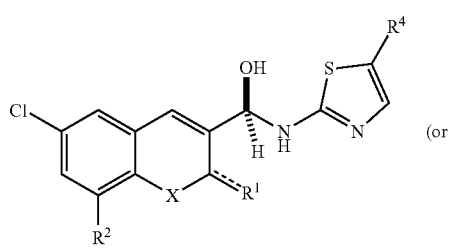

(or

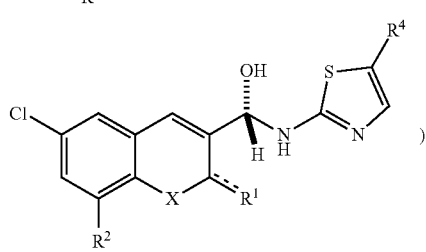

)

indicates either, or both, of the enantiomers below:

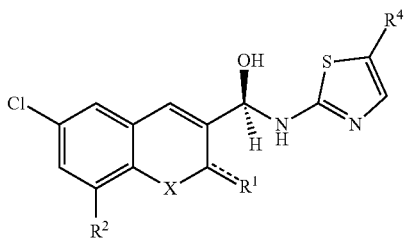

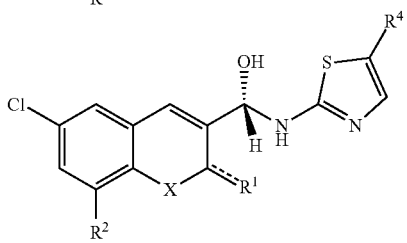

in any ratio, from pure enantiomers to racemates. The graphic representation:

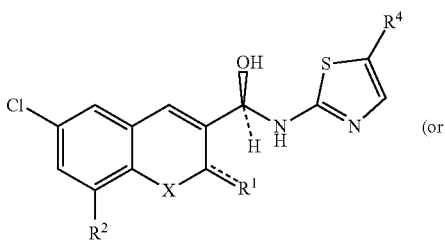

(or

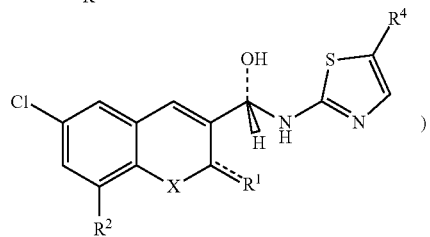

)

indicates a single enantiomer of unknown absolute stereochemistry, i.e. it could be either of the two preceding structures, as a substantially pure single enantiomer.

For the purpose of the present disclosure, a "pure" or "substantially pure" enantiomer is intended to mean that the enantiomer is at least 95% of the configuration shown and 5% or less of other enantiomers. Similarly, a "pure" or "substantially pure" diastereomer is intended to mean that the diastereomer is at least 95% of the relative configuration shown and 5% or less of other diastereomers.

It may be found upon examination that certain species and genera are not patentable to the inventors in this application. In this case, the exclusion of species and genera in applicants' claims are to be considered artifacts of patent prosecution and not reflective of the inventors' concept or description of their invention, which encompasses all members of the genus that are not in the public's possession.

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Also provided herein is a pharmaceutical composition comprising a compound disclosed above, or a pharmaceutically acceptable salt form thereof, and a pharmaceutically acceptable carrier or diluent.

While it may be possible for the compounds of the formulae disclosed herein to be administered as the raw chemical, it is preferable to present them as a pharmaceutical composition. According to a further aspect, the present invention provides a pharmaceutical composition comprising a compound of formula I or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2H$, $^3H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Compounds and compositions of the invention are useful for the treatment of fibrosis and fibrotic diseases. Such fibrotic diseases include, but are not limited to, renal fibrosis, pulmonary fibrosis, cystic fibrosis, cirrhosis, fibrosis of the heart, mediastinal fibrosis, retroperitoneal cavity fibrosis, bone marrow fibrosis, hypertrophic scars, keloids, scleroderma, systemic sclerosis, Crohn's disease, Peyronie's disease, lupus nephritis, folic acid nephropathy, and fibrosis induced by radiation, infection, chemotherapeutic drugs, surgery, burns or inhalation.

Compounds and compositions of the invention are also useful for the treatment of chronic kidney disease, renal fibrosis, or chronic renal allograft injury.

Compounds and compositions of the invention are useful for the treatment of cancer. In some embodiments, the cancer is a solid malignancy. In some embodiments, the cancer is mediated by myeloid cells. In other embodiments, the cancer is mediated by B-cells. In some embodiments, the cancer is colon cancer. In other embodiments, the cancer is colorectal cancer. In other embodiments, the cancer is rectal cancer. In yet other embodiments, the cancer is stomach cancer. In still other embodiments, the cancer is breast cancer. In some embodiments, the cancer is triple-negative breast cancer. In some embodiments, the cancer is a hematological malignancy. In other embodiments, the cancer is chronic myeloid leukemia. In other embodiments, the cancer is acute lymphoblastic leukemia. In still other embodiments, the cancer is a myelodysplastic syndrome. In yet other embodiments, the cancer is multiple myeloma. In some embodiments, the cancer is a lymphoma. In other embodiments, the cancer is a B-cell lymphoma.

Compounds and compositions of the invention are useful for the treatment of an autoimmune or inflammatory disease. In some embodiments, the disease is rheumatoid arthritis. In other embodiments, the disease is chronic obstructive pulmonary disease.

Compounds and compositions of the invention are useful for the treatment of a disease or disorder caused by a virus. In some embodiments, the disease is HIV/AIDS.

Compounds and compositions of the invention are useful for treating diseases or disorders that involve the dysregulation of hematopoietic cell kinase (HCK) signaling.

Abbreviations and Definitions

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In the event that there is a plurality of definitions for terms cited herein, those in this section prevail unless otherwise stated.

The following abbreviations and terms have the indicated meanings throughout:
Ac=acetyl
Aq=aqueous
Boc=t-butyloxy carbonyl
Bu=butyl
c-=cyclo
CDI=1,1'-Carbonyldiimidazole
DCC=N,N'-Dicyclohexylcarbodiimide
DCM=dichloromethane=methylene chloride=$CH_2Cl_2$
DMAP=4-Dimethylaminopyridine
DMF=N,N-dimethylformamide
eq. or equiv.=equivalent(s)
Et=ethyl
GC=gas chromatography
hour(s)
Me=methyl
mesyl=methanesulfonyl
min.=minute(s)
Pg=protecting group
Ph=phenyl
RT or rt=room temperature
sat'd or sat.=saturated
t- or tert=tertiary
TFA=trifluoroacetic acid
THF=tetrahydrofuran
TMSCN=Trimethylsilyl cyanide
tosyl=p-toluenesulfonyl As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof, but only if the additional features, integers, steps, components or groups thereof do not materially alter the basic and novel characteristics of the claimed composition or method.

A "patient," as used herein, includes both humans and other animals, particularly mammals. Thus, the methods are applicable to both human therapy and veterinary applications. In some embodiments, the patient is a mammal, for example, a primate. In some embodiments, the patient is a human.

Treatment can involve administering a compound described herein to a patient diagnosed with a disease and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

The terms "administer", "administering" or "administration" in reference to a dosage form of the invention refers to the act of introducing the dosage form into the system of subject in need of treatment. When a dosage form of the invention is given in combination with one or more other active agents (in their respective dosage forms), "administration" and its variants are each understood to include concurrent and/or sequential introduction of the dosage form and the other active agents. Administration of any of the described dosage forms includes parallel administration, co-administration or sequential administration. In some situations, the therapies are administered at approximately the same time, e.g., within about a few seconds to a few hours of one another.

A "therapeutically effective" amount of a compound described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

Throughout this specification the terms and substituents retain their definitions.

Unless otherwise specified, alkyl (or alkylene) is intended to include linear, branched, or cyclic saturated hydrocarbon structures and combinations thereof. A combination would be, for example, cyclopropylmethyl. Unless otherwise specified, alkyl refers to alkyl groups from 1 to 20 carbon atoms, in some instances 1 to 10 carbon atoms, in some instances 1 to 6 carbon atoms, in some instances 1 to 4 carbon atoms, and in some instances 1 to 3 carbon atoms. Examples of alkyl groups include methyl, ethyl, propyl, isopropyl, cyclopropyl, n-butyl, s-butyl, t-butyl and the like. Cycloalkyl is a subset of alkyl and includes cyclic hydrocarbon groups of from 3 to 8 carbon atoms and, in some instances, from 3 to 6 carbon atoms. Examples of cycloalkyl groups include c-propyl, c-butyl, c-pentyl, norbornyl and the like.

Heterocycle means a cycloalkyl or aryl carbocycle residue in which from one to four carbons is replaced by a heteroatom selected from the group consisting of N, O and S. The nitrogen and sulfur heteroatoms may optionally be oxidized, and the nitrogen heteroatom may optionally be quaternized. Unless otherwise specified, a heterocycle may be non-aromatic or aromatic. Examples of heterocycles that fall within the scope of the invention include pyrrolidine, piperidine, piperazine, azepane, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

Heteroaryl is a subset of heterocycle in which the heterocycle is aromatic. In some instances, the heteroaryl contains five or six ring members. Examples of these include isoxazole, oxazole, thiazole, furan, pyrazole, thiophene, thiazole, pyrrole, imidazole, isothiazole, oxadiazole, triazole, thiadiazole, pyridine, pyridazine, pyrimidine, pyrazine, and triazine, and the like. In some instances, heteroaryl may include isoxazole, oxazole, imidazole, and pyrazole.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like. Lower-alkoxy refers to groups containing one to four carbons. For the purpose of this application, alkoxy and lower alkoxy include methylenedioxy and ethylenedioxy.

The term "halogen" means fluorine, chlorine, bromine or iodine atoms. In one embodiment, halogen may be a fluorine or chlorine atom.

The terms "haloalkyl" and "haloalkoxy" mean alkyl or alkoxy, respectively, substituted with one or more halogen atoms.

Amidoxime refers to groups with the structure $R^A C(=NOH)NR^B R^C$. In some embodiments, at least one of $R^B$ and $R^C$ is hydrogen. In some embodiments, both $R^B$ and $R^C$ are hydrogen.

As used herein, the term "optionally substituted" may be used interchangeably with "unsubstituted or substituted". The term "substituted" refers to the replacement of one or more hydrogen atoms in a specified group with a specified radical. For example, unless otherwise specified, substituted alkyl, aryl, cycloalkyl, heterocyclyl, etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, di alkylaminoalkoxy, heterocyclylalkoxy, mercapto, alkylthio, sulfoxide, sulfone, sulfonylamino, alkylsulfinyl, alkyl sulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In some embodiments, substituents are halogen, haloalkyl, alkyl, acyl, hydroxyalkyl, hydroxy, alkoxy, haloalkoxy, aminocarbonyl oxaalkyl, carboxy, cyano, acetoxy, nitro, amino, alkylamino, dialkylamino, alkylthio, alkylsulfinyl, alkyl sulfonyl, alkylsulfonylamino aryl sulfonyl, arylsulfonylamino, and benzyloxy.

EXAMPLES

TABLE

| Example No. | Structure |
|---|---|
| 1 | 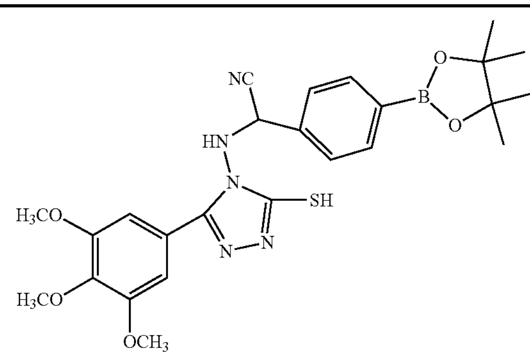 |

TABLE-continued
| Example No. | Structure |
|---|---|
| 2 | 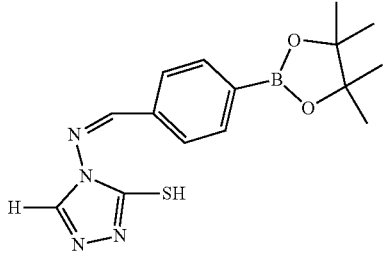 [SMILES: CC1(C)OB(c2ccc(/C=N\n3cnnc3S)cc2)OC1(C)C] |
| 3 | 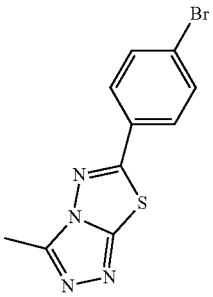 [SMILES: Cc1nnc2sc(-c3ccc(Br)cc3)nn12] |
| 4 | 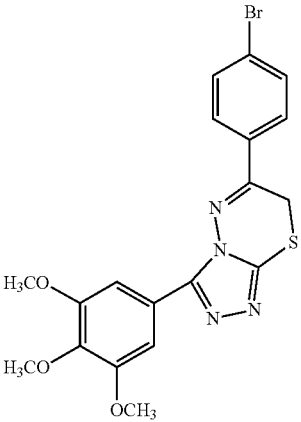 [SMILES: COc1cc(-c2nnc3n2N=C(c2ccc(Br)cc2)CS3)cc(OC)c1OC] |
| 5 | 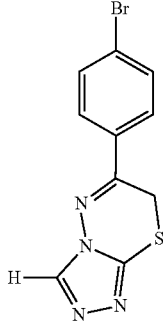 [SMILES: Brc1ccc(C2=Nn3cnnc3SC2)cc1] |
| 6 | 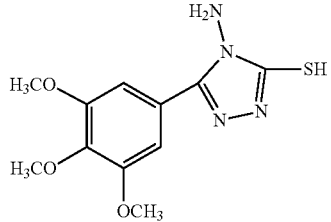 [SMILES: COc1cc(-c2nnc(S)n2N)cc(OC)c1OC] |

TABLE-continued

| Example No. | Structure |
|---|---|
| 7 | 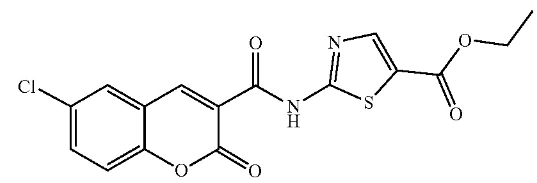 [SMILES: CCOC(=O)c1cnc(NC(=O)c2cc3cc(Cl)ccc3oc2=O)s1] |
| 8 | 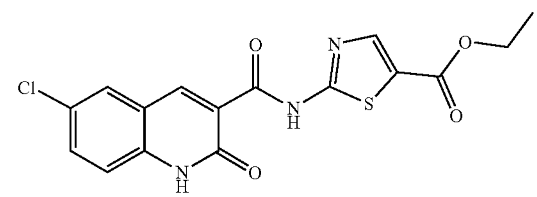 [SMILES: CCOC(=O)c1cnc(NC(=O)c2cc3cc(Cl)ccc3[nH]c2=O)s1] |
| 9 | 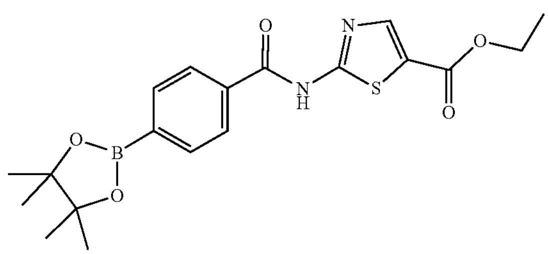 [SMILES: CCOC(=O)c1cnc(NC(=O)c2ccc(B3OC(C)(C)C(C)(C)O3)cc2)s1] |
| 10 | 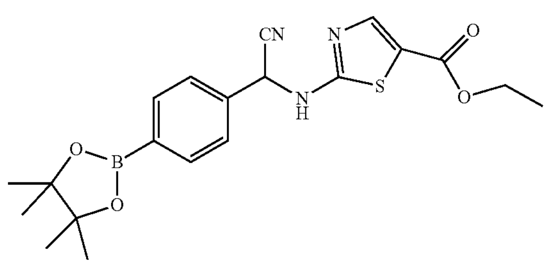 [SMILES: CCOC(=O)c1cnc(NC(C#N)c2ccc(B3OC(C)(C)C(C)(C)O3)cc2)s1] |
| 11 | 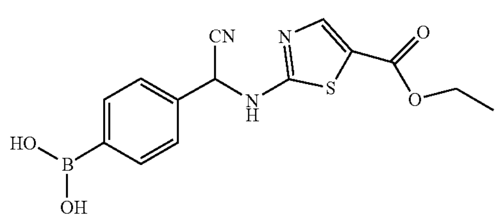 [SMILES: CCOC(=O)c1cnc(NC(C#N)c2ccc(B(O)O)cc2)s1] |
| 12 | 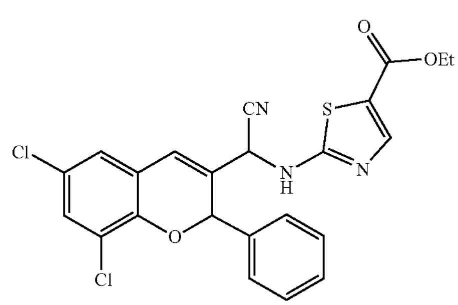 [SMILES: CCOC(=O)c1cnc(NC(C#N)C2=Cc3cc(Cl)cc(Cl)c3OC2c2ccccc2)s1] |

TABLE-continued
| Example No. | Structure |
|---|---|
| 13 | 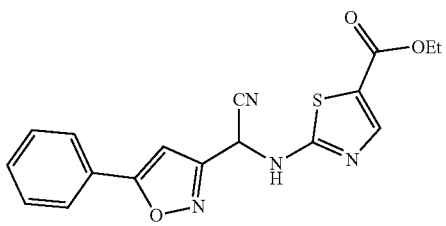 [SMILES: CCOC(=O)c1cnc(NC(C#N)c2cc(-c3ccccc3)on2)s1] |
| 14 | 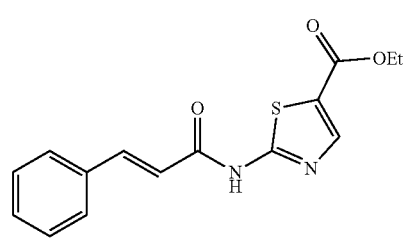 [SMILES: CCOC(=O)c1cnc(NC(=O)/C=C/c2ccccc2)s1] |
| 15 | 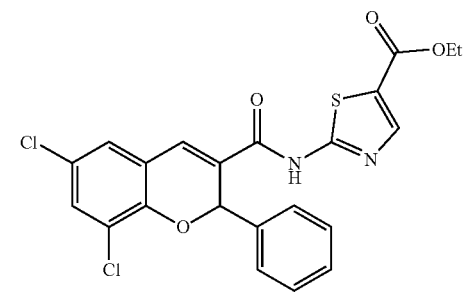 [SMILES: CCOC(=O)c1cnc(NC(=O)C2=Cc3cc(Cl)cc(Cl)c3OC2c2ccccc2)s1] |
| 16 | 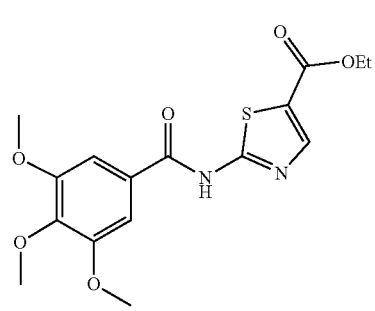 [SMILES: CCOC(=O)c1cnc(NC(=O)c2cc(OC)c(OC)c(OC)c2)s1] |
| 17 | 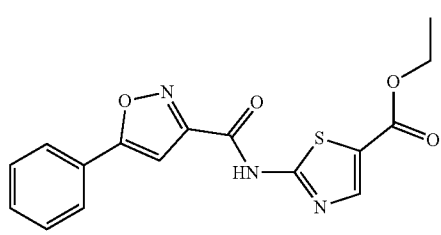 [SMILES: CCOC(=O)c1cnc(NC(=O)c2cc(-c3ccccc3)on2)s1] |

TABLE-continued

| Example No. | Structure |
|---|---|
| 18 | 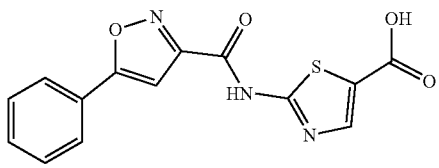 [SMILES: O=C(Nc1ncc(C(=O)O)s1)c1cc(-c2ccccc2)on1] |
| 19 | 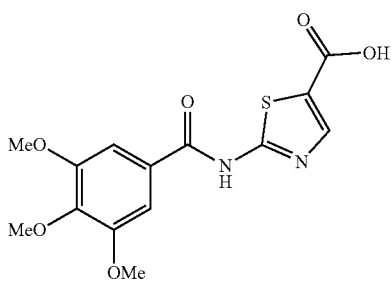 [SMILES: COc1cc(C(=O)Nc2ncc(C(=O)O)s2)cc(OC)c1OC] |
| 20 | 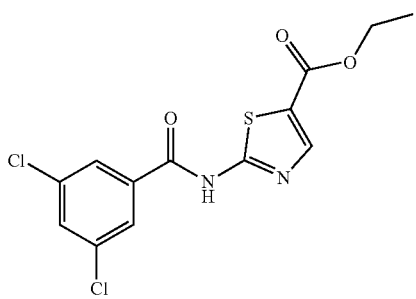 [SMILES: CCOC(=O)c1cnc(NC(=O)c2cc(Cl)cc(Cl)c2)s1] |
| 21 | 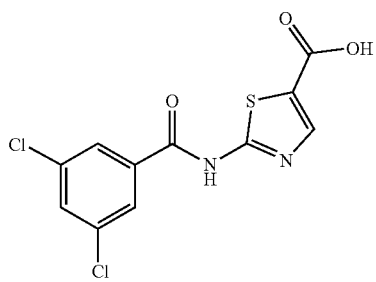 [SMILES: O=C(Nc1ncc(C(=O)O)s1)c1cc(Cl)cc(Cl)c1] |

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in Protecting Group Chemistry, 1$^{st}$ Ed., Oxford University Press, 2000; and in March's Advanced Organic chemistry: Reactions, Mechanisms, and Structure, 5$^{th}$ Ed., Wiley-Interscience Publication, 2001.

Many compounds described herein may be prepared by the schemes below:

Example No. 1—Synthesis of Example 1
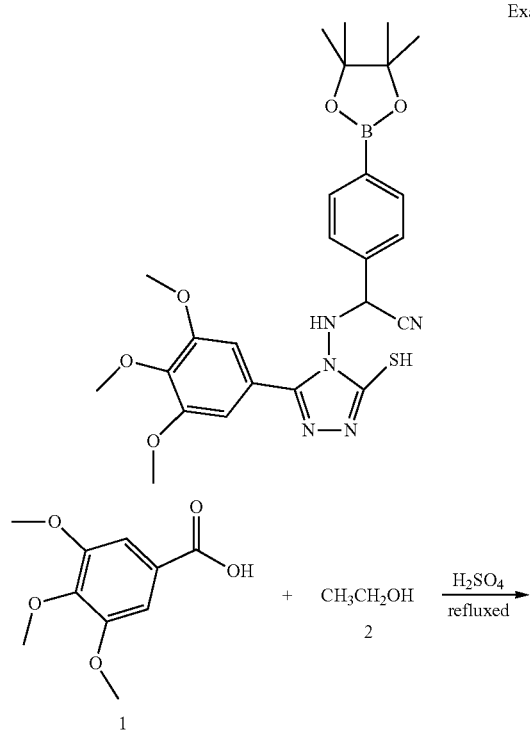
a) Synthesis of Compound 3
3,4,5-trimethoxybenzoic acid 1 (10.60 g, 0.05 mol) was dissolved in 50 ml EtOH 2, then H$_2$SO$_4$ (2.85 ml, 0.05 mol) was added, the reaction solution was refluxed overnight. The reaction was monitored by TLC until the starting material disappeared, the reaction was cooled down to room temperature and the precipitate was collected and washed by cold EtOH (95%). The solid compound 3 was recrystallized from EtOH to give pure product as white solid (10.92 g, 91%). $^1$H NMR (400 MHz; CDCl$_3$) δ 1.26 (3H, t, J=8), 3.91 (3H, s), 3.92 (6H, s), 4.38 (2H, q, J=8 Hz), 7.31 (2H, s); $^{13}$C NMR (200 MHz; CDCl$_3$) δ 14.4, 56.2, 60.9, 61.1, 106.7, 125.5, 141.9, 152.9, 166.2.

b) Synthesis of Compound 5

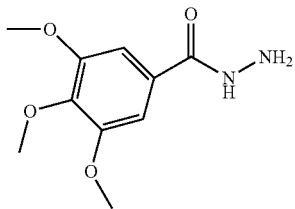

5

Ethyl 3,4,5-trimethoxybenzoate 3 (2.40 g, 0.01 mol) was dissolved in EtOH, then hydrazide hydrate 4 (1.93 ml, 0.04 mol) was added slowly with gentle stirring. After the addition was complete, the reaction solution was refluxed overnight and the reaction was monitored by TLC until starting material disappeared. Then the reaction was cooled down to room temperature, the precipitate was filtered off and crystallized from alcohol to give product 5 (2.0 g, 90%). $^1$H NMR (400 MHz; CDCl$_3$) δ 3.65 (3H, s), 3.66 (6H, s), 4.44 (1H, s), 7.16 (2H, s), 9.69 (1H, s). $^{13}$C NMR (200 MHz; CDCl$_3$) δ 56.4, 60.5, 104.4, 128.9, 140.1, 153.0, 165.8.

c) Synthesis of Compound 7

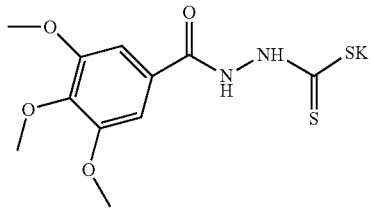

7

3,4,5-trimethoxybenzohydrazide 5 (2.26 g, 0.01 mol) was added to EtOH (50 ml), to the suspension solution, Potassium hydroxide (0.84 g, 0.015 mol) was added and the solution was stirred until the entire solution was clear, then carbon disulfide (0.90 ml, 0.015 mol) was added dropwise. Then the reaction was stirred at room temperature for 24 hours. And the solvent was removed and the solid was used directly for next step.

d) Synthesis of Compound 8

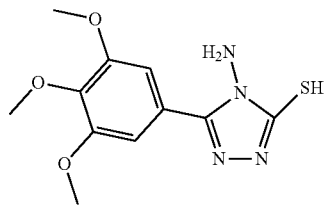

8

Potassium salt 7 obtained from the previous step was suspended in alcohol, hydrazide hydrate (1.0 ml, 0.02 mol) was added, followed by adding 3.0 ml of H$_2$O, the solution was refluxed overnight, the solution turned greenish with evolution of hydrogen sulfide gas, then the solution was diluted by adding 50 ml of H$_2$O and the solution was acidified with concentrated HCl. The resulting white precipitate was filtered and washed with cold water and air dried. The product was purified by recrystallization in alcohol, compound 8 (1.69, 60%). $^1$H NMR (400 MHz; DMSO-d6) δ 3.70 (3H, s), 3.80 (6H, s), 5.82 (2H, s), 7.32 (2H, s), 13.93 (1H, s); $^{13}$C NMR (200 MHz; DMSO-d6) δ 56.5, 60.6, 106.2, 121.4, 139.7, 149.6, 153.2, 167.0.

e) Synthesis of Example 1

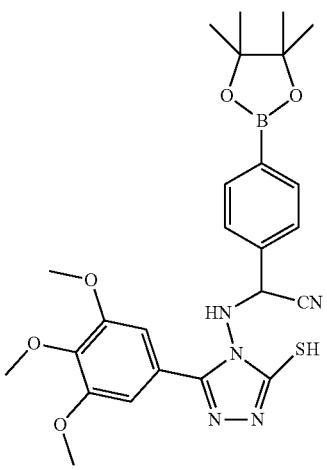

Example 1

A mixture of 4-amino-5-(3,4,5-trimethoxyphenyl)-4H-1,2,4-triazole-3-thiol 8 (155.5 mg, 0.55 mmol), 4-formylphenylboronic acid, pinacol ester 9 (purchased from Aldrich) (127.67 mg, 0.55 mmol) and InCl$_3$ (24.7 mg, 0.11 mmol) was dissolved in acetonitrile, the TMSCN (82.6 μl, 0.66 mmol) was injected under argon. The reaction solution was stirred under room temperature overnight. Then the acetonitrile was evaporated and the solid was dissolved in ethyl acetate and washed with water, brine and dried over Na$_2$SO$_4$. After removing the solvent, the solid was recrystallized from alcohol to give pure product (0.22 mg, 75%). $^1$H NMR (400 MHz; DMSO-d6) δ 1.29 (12H, s), 3.69 (3H, s), 3.74 (6H, s), 7.20 (2H, s), 7.82 (2H, dd), 7.91 (2H, dd), 9.73 (1H, s); $^{13}$C NMR (200 MHz; DMSO-d6) δ 56.4, 60.6, 104.6, 106.2, 120.9, 128.3, 134.8, 135.5, 139.8, 148.6, 153.3, 162.7, 166.7.

Example No. 2—Synthesis of Compound Example 2 a) Synthesis of Compound 3

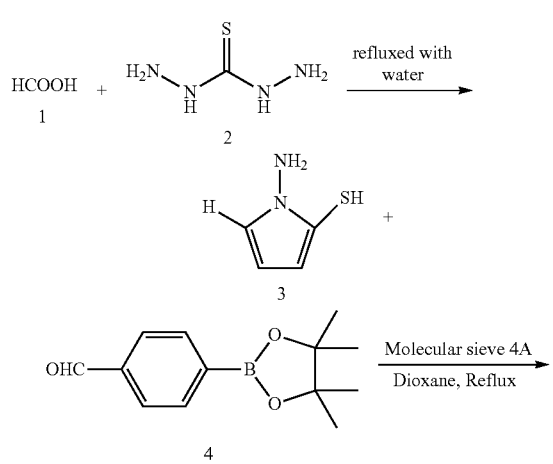

Thiocarbohydrazide 2 (2.0 g, 18.8 mmol) and formic acid 1 (1.5 ml, 40.0 mmol) was mixed in a round flask, 6 ml of H$_2$O was added. The reaction solution was refluxed overnight and cooled to room temperature, a lot of white solid precipitated from solution. The solid was filtered and air dried to give product 3 (1.2 g, 54%). $^1$H NMR (400 MHz; DMSO-d6) δ 5.66 (2H, s), 8.43 (1H, s), 13.63 (1H, s); $^{13}$C NMR (200 MHz; DMSO-d6) δ 161.7, 131.9.

b) Synthesis of Example 2

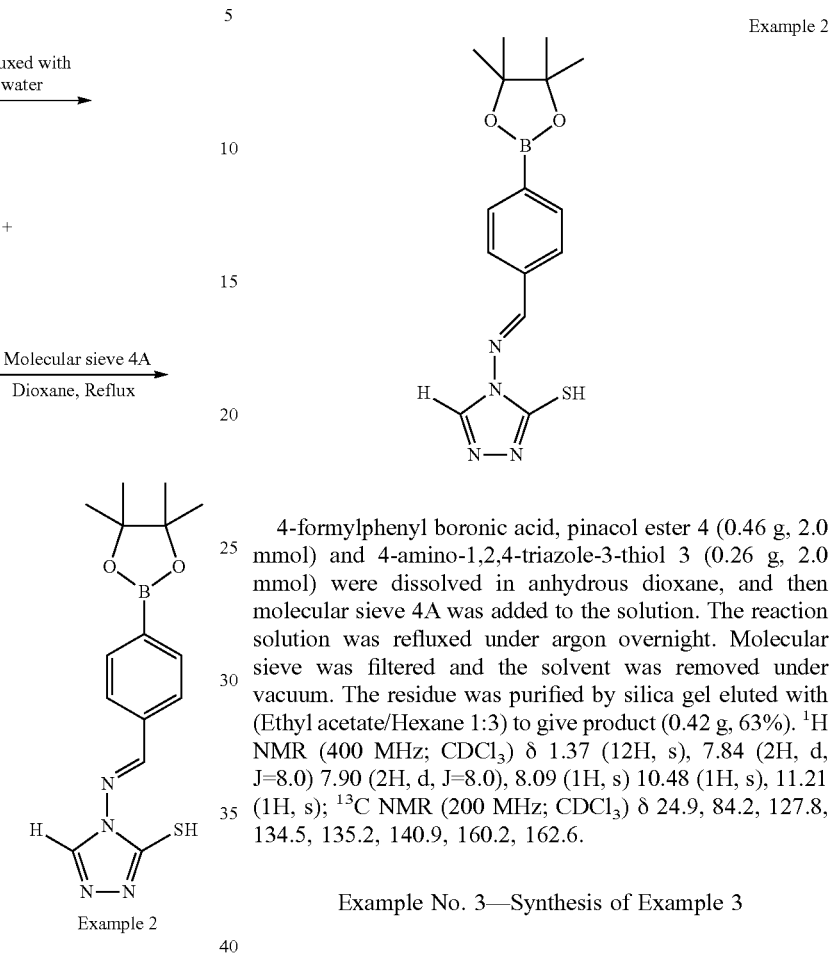

4-formylphenyl boronic acid, pinacol ester 4 (0.46 g, 2.0 mmol) and 4-amino-1,2,4-triazole-3-thiol 3 (0.26 g, 2.0 mmol) were dissolved in anhydrous dioxane, and then molecular sieve 4A was added to the solution. The reaction solution was refluxed under argon overnight. Molecular sieve was filtered and the solvent was removed under vacuum. The residue was purified by silica gel eluted with (Ethyl acetate/Hexane 1:3) to give product (0.42 g, 63%). $^1$H NMR (400 MHz; CDCl$_3$) δ 1.37 (12H, s), 7.84 (2H, d, J=8.0) 7.90 (2H, d, J=8.0), 8.09 (1H, s) 10.48 (1H, s), 11.21 (1H, s); $^{13}$C NMR (200 MHz; CDCl$_3$) δ 24.9, 84.2, 127.8, 134.5, 135.2, 140.9, 160.2, 162.6.

Example No. 3—Synthesis of Example 3 a) Synthesis of Compound 3

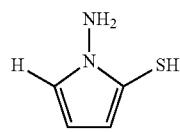

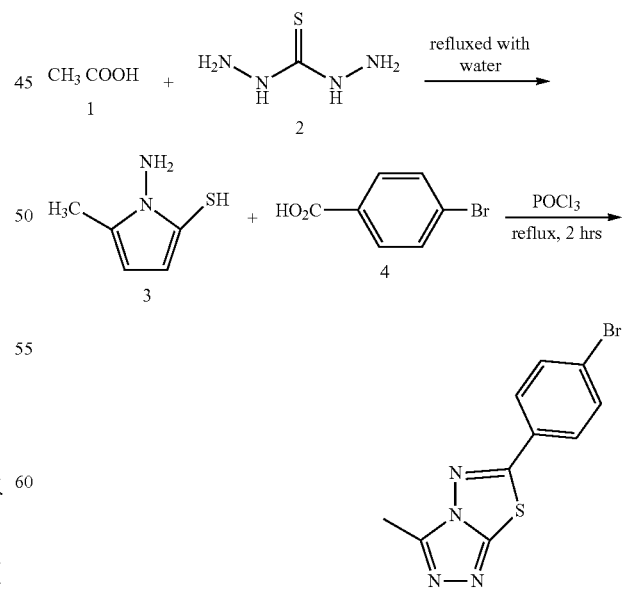

a) Synthesis of Compound 3

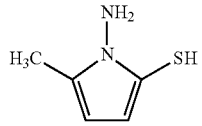
3

Thiocarbohydrazide 2 (2.0 g, 18.8 mmol) and acetic acid 1 (4.0 ml, 70 mmol) were mixed in a round flask. The reaction solution was refluxed overnight and cooled to room temperature, and the precipitate was filtered and air dried to give product (1.7 g, 70%). $^1$H NMR (400 MHz; DMSO-d6) δ 2.21 (3H, s), 5.51 (2H, s), 13.40 (1H, s); $^{13}$C NMR (200 MHz; DMSO-d6) δ 10.9, 149.6, 165.8.

b) Synthesis of Compound Example 3

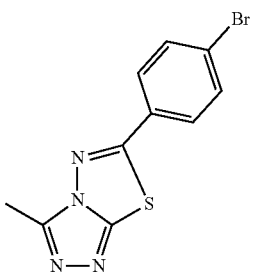
Example 3

4-amino-1,2,4-triazole-3-thiol 3 (0.26 g, 2.0 mmol) and 4-bromobenzoic acid 4 (0.40 g, 2.0 mmol) was dissolved in 10 ml phosphorus oxychloride. The suspension solution was heated to 110° C. and refluxed for 3 hours, then the phosphorus oxychloride was removed under vacuum. The solid was washed with water and NaHCO$_3$, and air dried. The product was recrystallized from alcohol to give product (0.47 g, 81%). $^1$H NMR (400 MHz; CDCl$_3$) δ 2.77 (3H, s), 7.68 (2H, d, J=8.0), 7.76 (2H, d, J=8.0); $^{13}$C NMR (200 MHz; CDCl$_3$) δ 10.5, 127.3, 128.2, 132.5, 144.8, 152.5, 165.2.

Example No. 4—Synthesis of Example 4

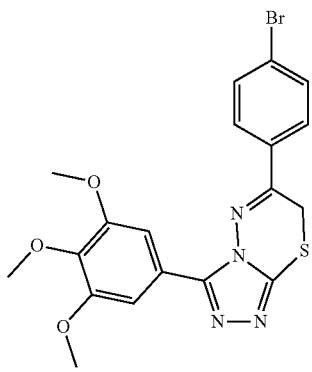
Example 4

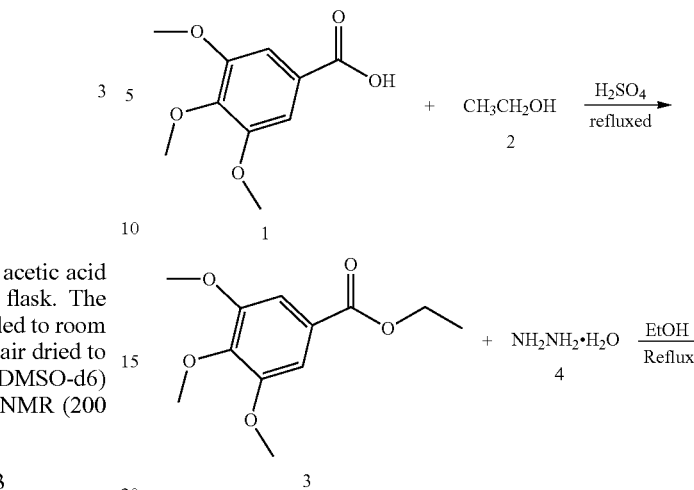

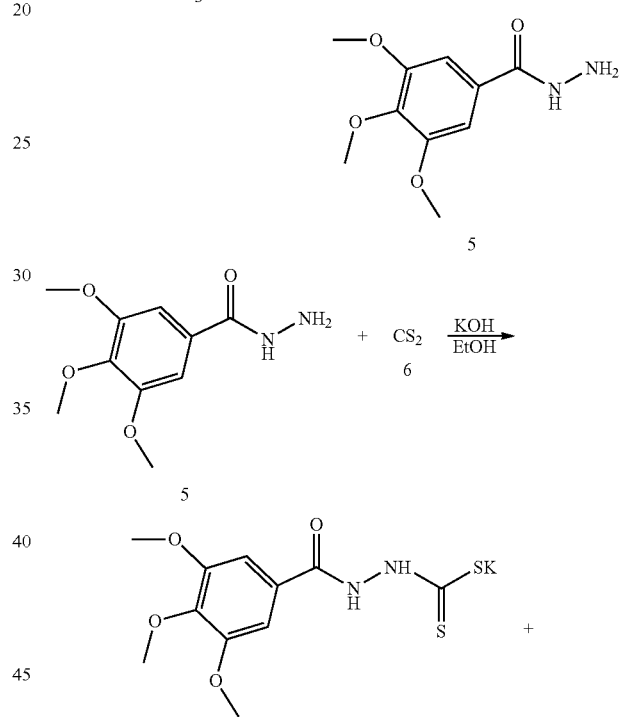

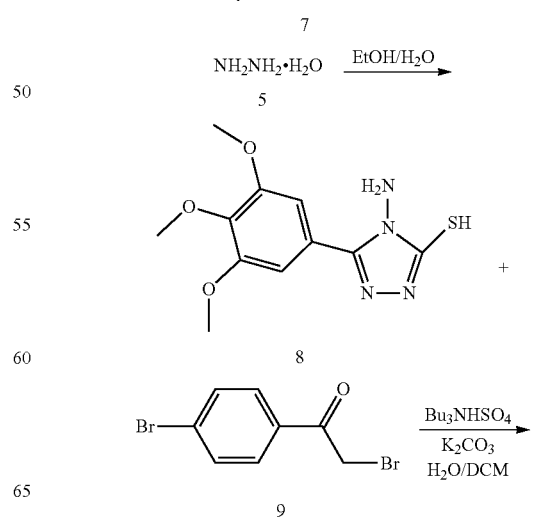

Example 4 a) Synthesis of Compound 3

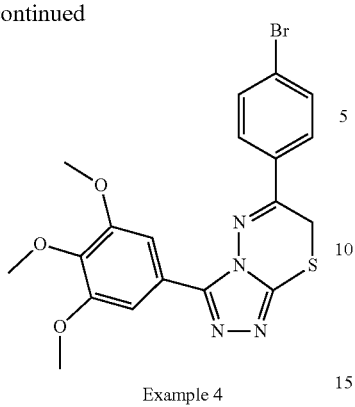

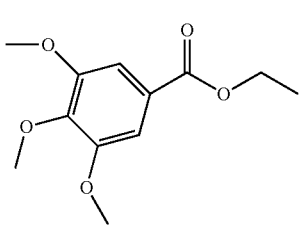

3,4,5-trimethoxybenzoic acid 1 (10.60 g, 0.05 mol) was dissolved in 50 ml EtOH 2, then H$_2$SO$_4$ (2.85 ml, 0.05 mol) was added, and the reaction solution was refluxed overnight. The reaction was monitored by TLC until the starting material disappeared, the reaction was cooled down to room temperature and the precipitate was collected and washed by cold EtOH (95%). The solid compound 3 was recrystallized from EtOH to give pure product as white solid (10.92 g, 91%). $^1$H NMR (400 MHz; CDCl$_3$) δ 1.26 (3H, t, J=8), 3.91 (3H, s), 3.92 (6H, s), 4.38 (2H, q, J=8 Hz), 7.31 (2H, s); $^{13}$C NMR (200 MHz; CDCl$_3$) δ 14.4, 56.2, 60.9, 61.1, 106.7, 125.5, 141.9, 152.9, 166.2.

b) Synthesis of Compound 5

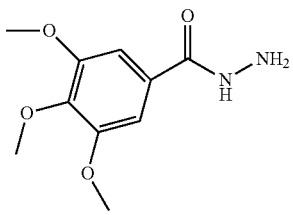

Ethyl 3,4,5-trimethoxybenzoate 3 (2.40 g, 0.01 mol) was dissolved in EtOH, then hydrazide hydrate 4 (1.93 ml, 0.04 mol) was added slowly with gentle stirring. After the addition was complete, the reaction solution was refluxed overnight and the reaction was monitored by TLC until starting material disappeared. Then the reaction was cooled down to room temperature, the precipitate was filtered and crystallized from alcohol to give product 5 (2.0 g, 90%). $^1$H NMR (400 MHz; CDCl$_3$) δ 3.65 (3H, s), 3.66 (6H, s), 4.44 (1H, s), 7.16 (2H, s), 9.69 (1H, s). $^{13}$C NMR (200 MHz; CDCl$_3$) δ 56.4, 60.5, 104.4, 128.9, 140.1, 153.0, 165.8.

c) Synthesis of Compound 7

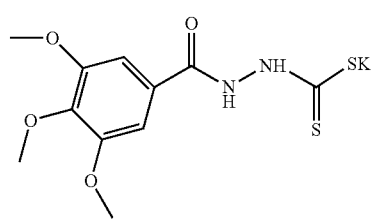

3,4,5-trimethoxybenzohydrazide 5 (2.26 g, 0.01 mol) was added to EtOH (50 ml), to the suspension solution, Potassium hydroxide (0.84 g, 0.015 mol) was added and the solution was stirred until the entire solution was clear, then carbon disulfide (0.90 ml, 0.015 mol) was added dropwise. Then the reaction was stirred at room temperature for 24 hours. And the solvent was removed and the solid was used directly for next step.

d) Synthesis of Compound 8

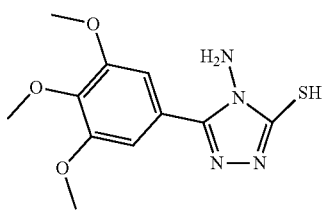

Potassium salt 7 obtained from the previous step was suspended in alcohol; hydrazide hydrate (1.0 ml, 0.02 mol) was added, followed by adding 3.0 ml of H$_2$O. The solution was refluxed overnight; the solution turned greenish with evolution of hydrogen sulfide gas, then the solution was diluted by adding 50 ml of H$_2$O and the solution was acidified with concentrated HCl. The resulting white precipitate was filtered and washed with cold water and air dried. The product was purified by recrystallization in alcohol, compound 8 (1.69, 60%). $^1$H NMR (400 MHz; DMSO-d6) δ 3.70 (3H, s), 3.80 (6H, s), 5.82 (2H, s), 7.32 (2H, s), 13.93 (1H, s); $^{13}$C NMR (200 MHz; DMSO-d6) δ 56.5, 60.6, 106.2, 121.4, 139.7, 149.6, 153.2, 167.0.

e) Synthesis of Example 4

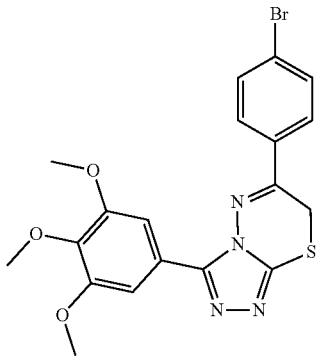

Example 4

4-amino-5-(3,4,5-trimethoxyphenyl)-4H-1,2,4-triazole-3-thiol 8 (Example 6) (0.56 g, 2.0 mmol), tetrabutylammonium hydrogen sulfate (0.34 g, 1.0 mmol) and $K_2CO_3$ (0.56 g, 4.0 mmol) were added to a round flask, then 5 ml of water was added to dissolve the mixture, followed by adding 20 ml dichloromethane. The solution was stirred for 10 minutes, then the solution of 2,4-dibromoacetophenone 9 (0.56 g, 2.0 mmol) in 10 ml dichloromethane was added. The reaction solution was stirred overnight, then diluted with water. The solution was extracted by dichloromethane three times and the organic layer was combined and washed by 1 M HCl, $H_2O$ and brine. Then the solution was dried over $Na_2SO_4$ and the solvent was removed. The product was purified by silica gel eluted with ethyl acetate/hexane (1:2) to give Example 4 (0.74 g, 80%). $^1$H NMR (400 MHz; DMSO-d6) δ 3.73 (3H, s), 3.82 (6H, s), 4.41 (2H, s), 7.34 (2H, s), 7.80 (2H, d, J=8.0), 7.98 (2H, d, J=8.0); $^{13}$C NMR (200 MHz; DMSO-d6) δ 56.4, 60.6, 105.7, 121.6, 126.3, 129.8, 132.6, 133.0, 139.5, 142.7, 151.6, 153.4, 155.4.

Example No. 5—Synthesis of Example 5

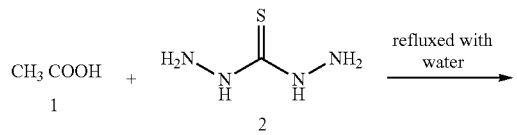

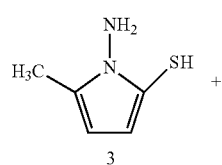

a) Synthesis of Compound 3

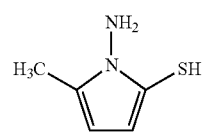

3

Thiocarbohydrazide 2 (2.0 g, 18.8 mmol) and acetic acid 1 (4.0 ml, 70 mmol) were mixed in a round flask. The reaction solution was refluxed overnight and cooled to room temperature, the precipitate was filtered and air dried to give product (1.7 g, 70%). $^1$H NMR (400 MHz; DMSO-d6) δ 2.21 (3H, s), 5.51 (2H, s), 13.40 (1H, s); $^{13}$C NMR (200 MHz; DMSO-d6) δ 10.9, 149.6, 165.8.

b) Synthesis of Example 5

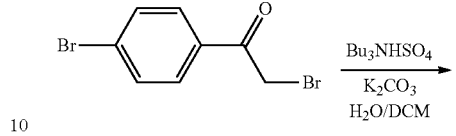

Example 5

4-amino-1,2,4-triazole-3-thiol (0.65 g, 5.0 mmol), tetrabutylammonium hydrogen sulfate (0.85 g, 2.5 mmol) and $K_2CO_3$ (1.38 g, 10 mmol) were added to a round flask, then 5 ml of $H_2O$ was added. When the solution became clear, 20 ml of DCM was added. The reaction solution was stirred vigorously for 10 minutes before 2,4-dibromoacetophenone (1.39 g, 5.0 mmol) in 20 ml of DCM was added. The solution was stirred overnight and diluted by 30 ml of $H_2O$ and then extracted by DCM for three times. The organic layers were combined and washed with water, brine and dried over $Na_2SO_4$. The solvent was removed under vacuum and the product was recrystallized from alcohol to give product (1.2 g, 80%). $^1$H NMR (400 MHz; DMSO-d6) δ

2.05 (3H, s), 4.34 (2H, s), 7.75 (2H, d, J=8.0), 7.92 (2H, d, J=8.0); $^{13}$C NMR (200 MHz; DMSO-d6) δ 10.3, 23.2, 126.1, 129.8, 132.5, 133.2, 140.2, 150.9, 154.3.

Example No. 6—Synthesis of Example 6

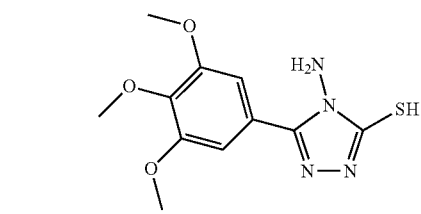

Example 6

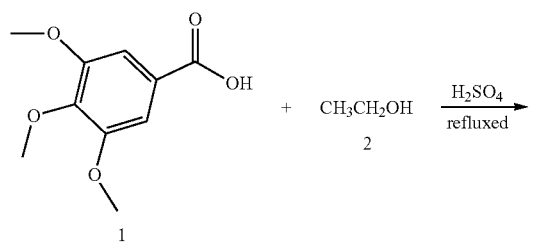

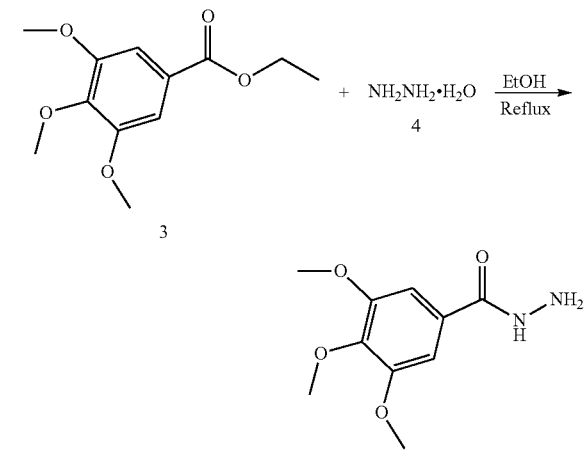

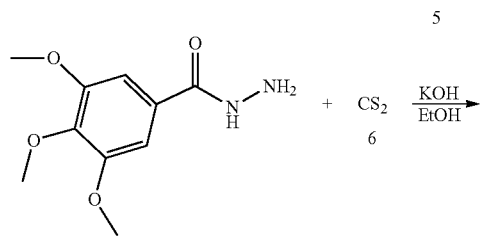

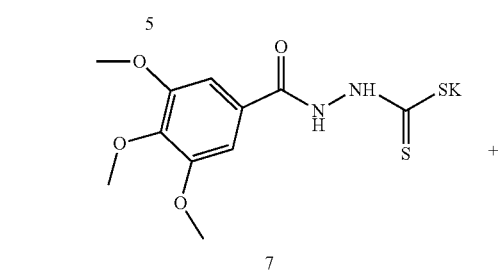

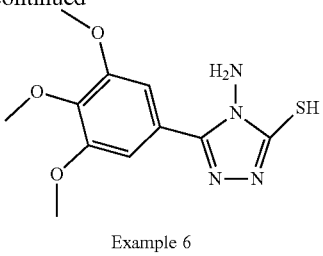

Example 6 a) Synthesis of Compound 3

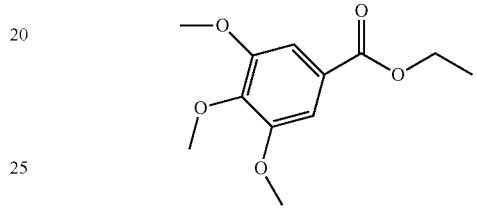

3,4,5-trimethoxybenzoic acid 1 (10.60 g, 0.05 mol) was dissolved in 50 ml EtOH 2, then H$_2$SO$_4$ (2.85 ml, 0.05 mol) was added; the reaction solution was refluxed overnight. The reaction was monitored by TLC until the starting material disappeared. The reaction was cooled down to room temperature and the precipitate was collected and washed by cold EtOH (95%). The solid compound 3 was recrystallized from EtOH to give pure product as white solid (10.92 g, 91%). $^1$H NMR (400 MHz; CDCl$_3$) δ 1.26 (3H, t, J=8), 3.91 (3H, s), 3.92 (6H, s), 4.38 (2H, q, J=8 Hz), 7.31 (2H, s); $^{13}$C NMR (200 MHz; CDCl$_3$) δ 14.4, 56.2, 60.9, 61.1, 106.7, 125.5, 141.9, 152.9, 166.2.

b) Synthesis of Compound 5

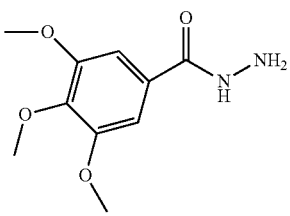

Ethyl 3,4,5-trimethoxybenzoate 3 (2.40 g, 0.01 mol) was dissolved in EtOH, then hydrazide hydrate 4 (1.93 ml, 0.04 mol) was added slowly with gentle stirring. After the addition was complete, the reaction solution was refluxed overnight and the reaction was monitored by TLC until the starting material disappeared. Then the reaction was cooled down to room temperature, the precipitate was filtered and crystallized from alcohol to give product 5 (2.0 g, 90%). $^1$H NMR (400 MHz; CDCl$_3$) δ 3.65 (3H, s), 3.66 (6H, s), 4.44 (1H, s), 7.16 (2H, s), 9.69 (1H, s). $^{13}$C NMR (200 MHz; CDCl$_3$) δ 56.4, 60.5, 104.4, 128.9, 140.1, 153.0, 165.8.

c) Synthesis of Compound 7

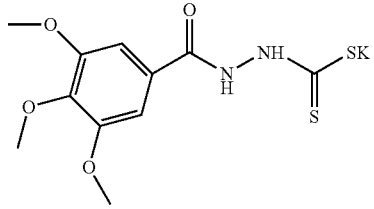

3,4,5-trimethoxybenzohydrazide 5 (2.26 g, 0.01 mol) was added to EtOH (50 ml). To the suspension solution, Potassium hydroxide (0.84 g, 0.015 mol) was added and the solution was stirred until the entire solution was clear, then carbon disulfide (0.90 ml, 0.015 mol) was added dropwise. The reaction was then stirred at room temperature for 24 hours. The solvent was removed and the solid was used directly for the next step.

d) Synthesis of Example 6

Example 6

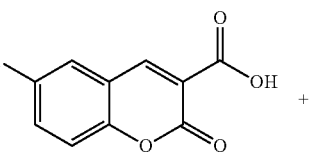

Potassium salt 7 obtained from the previous step was suspended in alcohol, hydrazide hydrate (1.0 ml, 0.02 mol) was added, followed by adding 3.0 ml of H$_2$O. The solution was refluxed overnight, the solution turned greenish with evolution of hydrogen sulfide gas, then the solution was diluted by adding 50 ml of H$_2$O and the solution was acidified with concentrated HCl. The resulting white precipitate was filtered and washed with cold water and air dried. The product was purified by recrystallization in alcohol. (1.69, 60%). $^1$H NMR (400 MHz; DMSO-d6) δ 3.70 (3H, s), 3.80 (6H, s), 5.82 (2H, s), 7.32 (2H, s), 13.93 (1H, s); $^{13}$C NMR (200 MHz; DMSO-d6) δ 56.5, 60.6, 106.2, 121.4, 139.7, 149.6, 153.2, 167.0.

Example No. 7—Synthesis of Example 7

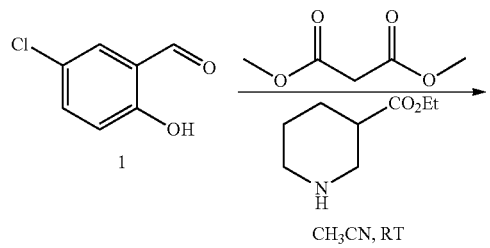

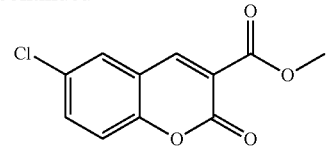

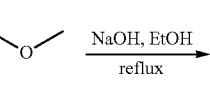

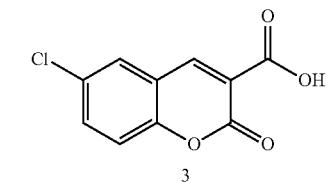

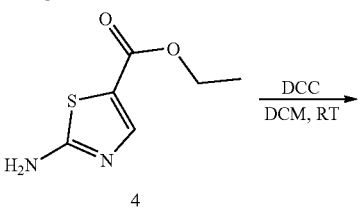

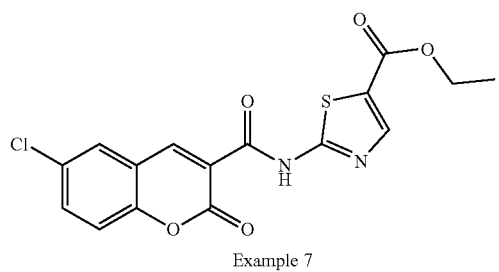

Example 7 a) Synthesis of Compound 2

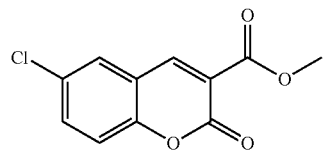

Procedure for synthesis of Methyl 6-chloro-2-oxo-2H-chromene-3-carboxylate: 5-chlorosalicylaldehyde (1.55 g, 10 mmol) was added into CH$_3$CN (5 mL) in a 35 mL reaction tube. To this dimethylmalonate (1.45 g, 11 mmol), ethyl piperdine-3-carboxylate (15 mg, 10 mol %) in 15 mL CH$_3$CN were added. The resultant reaction mixture was stirred at room temperature for 24 hrs. After evaporation of the acetonitrile, the crude reaction mixture was purified by a silica gel chromatography to give a white solid 1 (1.6 g, 60%). ¹H NMR (DMSO, 600 MHz) δ 8.71 (s, 1H), 8.01 (s, 1H), 7.75 (d, J=9.6 Hz, 1H), 7.45 (d, J=9.3 Hz, 1H), 3.82 (s, 3H) ppm; ¹³C NMR (DMSO, 75 MHz) δ 163.2, 161.9, 148.5, 147.7, 134.9, 134.3, 129.9, 128.4, 118.9, 118.4, 53.1 ppm. HRMS (EI) Calcd. for C11H7ClO4 [M+H]⁺ requires 239.0111, found 239.0117.

b) Synthesis of Compound 3

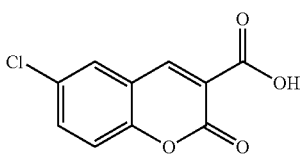

3

Procedure for synthesis of 6-chloro-2-oxo-2H-chromene-3-carboxylic acid: to a solution of methyl 6-chloro-2-oxo-2H-chromene-3-carboxylate (1.0 g, 4.2 mmmol) in ethanol was added sodium hydroxide (10% w/v in 20 mL ethanol). This mixture was stirred under reflux conditions for 24 hrs. Further after completion of the reaction, the reaction mixture was cooled down room temperature and diluted with 10% HCl. The solid precipitated out was isolated and washed with water to afford the product as a white solid (0.75 g, 80%). ¹H NMR (DMSO, 300 MHz) δ 13.38 (s, 1H), 8.68 (s, 1H), 8.02 (s, 1H), 7.74 (d, J=9 Hz, 1H), 7.46 (d, J=9 Hz, 1H) ppm; ¹³C NMR (DMSO, 75 MHz) δ 164.1, 156.5, 153.48, 128.8, 119.9, 119.7, 118.5, 111.48, 102.19 ppm. HRMS (EI) Calcd. for C10H5ClO4 [M+H]⁺ requires 224.9955, found 224.9948.

c) Synthesis of Example 7

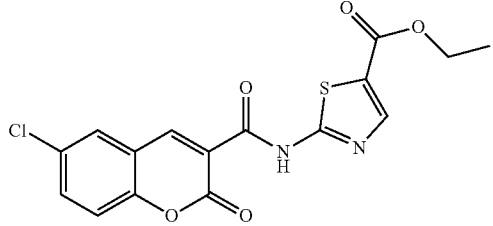

Example 7

The 6-chloro-2-oxo-2H-chromene-3-carboxylic acid (1.0 mmol) was dissolved in DCM (3 mL) in a 35 mL reaction tube. To this solution was added ethyl 2-aminothiazole-5-carboxylate (1.1 mmol) and CDI (1.2 mmol). The resultant reaction mixture was stirred at room temperature for 24 hrs. After completion of the reaction, the reaction was then quenched by saturated aq. NaOH solution, extracted with DCM (10×3 mL). The combined organic layers were dried over Na₂SO₄ and filtered. After evaporation of the organic solvent, the residue was purified by a silica gel chromatography to provide the product. ¹H NMR (DMSO, 300 MHz) δ 9.39 (s, 1H), 8.81 (s, 1H), 7.85 (d, J=2.4 Hz, 1H), 7.35 (dd, J₁=9 Hz, J₂=2.4 Hz, 1H), 7.13 (d, J=9 Hz, 2H), 7.02 (m, 1H), 4.5 (q, J=8 Hz, 2H), 1.47 (t, J=8 Hz, 3H) ppm. HRMS (ESI+): Calcd for C20H11ClN2O5S [M+H]: 377.0077, Found: 377.0133.

Example No. 8—Synthesis of Example 8

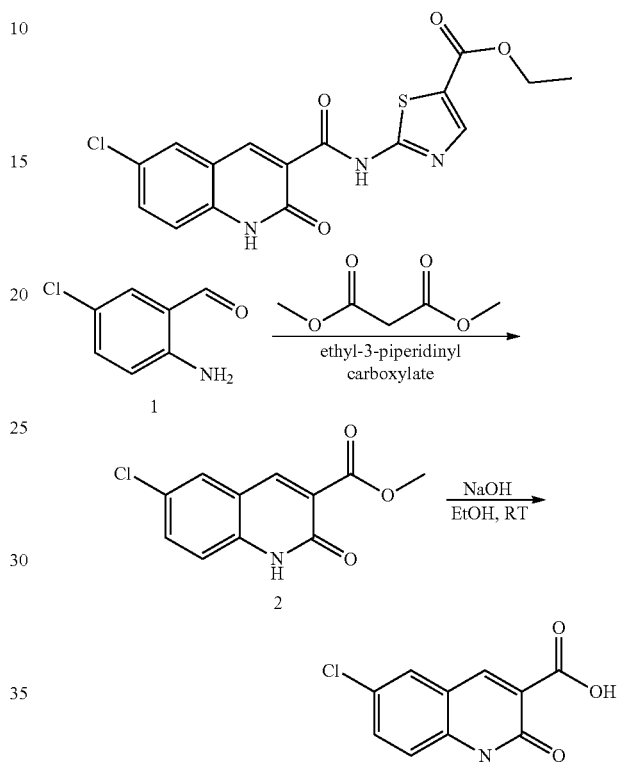

Example 8

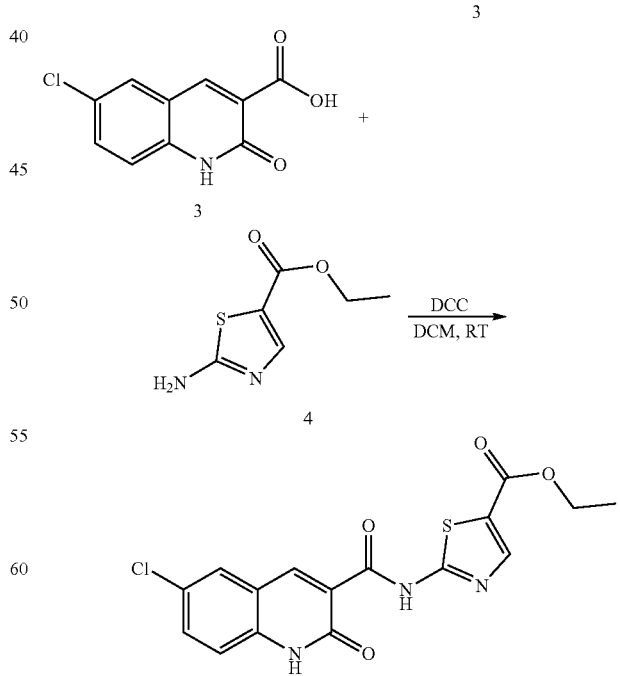

Example 8 a) Synthesis of Compound 2

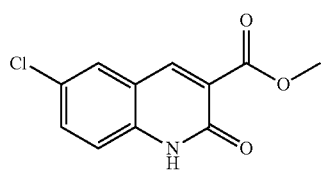

2

Procedure for synthesis of methyl 6-chloro-2-oxo-1,2-dihydroquinoline-3-carboxylate: 2-amino-5-chlorobenzaldehyde (1.55 g, 10 mmol) was added into CH₃CN (5 mL) in a 35 mL reaction tube. To this dimethylmalonate (1.45 g, 11 mmol), ethyl piperdine-3-carboxylate (15 mg, 10 mol %) in 15 mL CH₃CN were added. The resultant reaction mixture was stirred at room temperature for 24 hrs. After evaporation of the acetonitrile, the crude reaction mixture was purified by a silica gel chromatography to give a white solid 1 (1.12 g, 95%). $^1$H NMR (DMSO-d6, 600 MHz) δ 8.47 (s, 1H), 7.93 (d, J=2.4 Hz, 1H), 7.62 (dd, J1=9.0 Hz, J2=2.4 Hz, 1H), 7.3 (d, J=8.4 Hz, 1H), 3.78 (s, 3H) ppm; $^{13}$C NMR (DMSO-d6, 75 MHz) δ 165.1, 158.7, 143.3, 139.27, 132.9, 128.6, 126.4, 124.6, 119.2, 117.4, 52.6 ppm. HRMS (ESI+): Calcd for C20H18NO3 [M+]: 237.0193, Found: 316.0414.

b) Synthesis Procedure of Compound 3

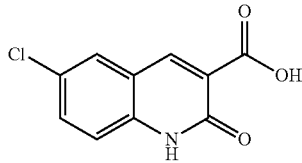

3

Procedure for synthesis of 6-chloro-2-oxo-1,2-dihydroquinoline-3-carboxylic acid: to a solution of methyl 6-chloro-2-oxo-1,2-dihydroquinoline-3-carboxylate (1.0 g, 4.2 mmmol) in ethanol was added sodium hydroxide (10% w/v in 20 mL ethanol). This mixture was stirred under reflux conditions for 24 hrs. Further after completion of the reaction, the reaction mixture was cooled down to room temperature and diluted with 10% HCl. The solid precipitated out was isolated and washed with water to afford the product as white solid (650 mg, 97%). $^1$H NMR (DMSO, 300 MHz) δ 13.24 (s, 1H), 8.9 (s, 1H), 8.16 (d, J=2.4 Hz, 1H), 7.78 (dd, J₁=9 Hz, J₂=2.4 Hz, 1H), 7.49 (d, J=9 Hz, 1H) ppm; $^{13}$C NMR (DMSO, 75 MHz) δ 164.7, 164.0, 145.7, 138.5, 134.1, 129.4, 128.0, 120.65, 119.4, 118.5 ppm. HRMS (ESI+): Calcd for C20H18N3O [M+H]: 224.0114, Found: 316.0105.

c) Synthesis Procedure of Example 8

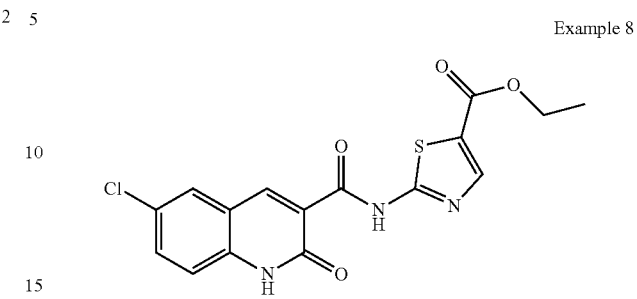

Example 8

The 6-chloro-2-oxo-1,2-dihydroquinoline-3-carboxylic acid (1.0 mmol) was dissolved in DCM (3 mL) in a 35 mL reaction tube. To this solution was added ethyl 2-aminothiazole-5-carboxylate (1.1 mmol) and CDI (1.2 mmol). The resultant reaction mixture was stirred at room temperature for 24 hrs. After completion of the reaction, the reaction was then quenched by saturated aq. NaOH solution and extracted with DCM (10×3 mL). The combined organic layers were dried over Na₂SO₄ and filtered. After evaporation of the organic solvent, the residue was purified by a silica gel chromatography to provide the product. $^1$H NMR (DMSO, 300 MHz) δ 9.39 (s, 1H), 8.81 (s, 1H), 7.85 (d, J=2.4 Hz, 1H), 7.35 (dd, J₁=9 Hz, J₂=2.4 Hz, 1H), 7.13 (d, J=9 Hz, 2H), 7.02 (m, 1H), 4.5 (q, J=8 Hz, 2H), 1.47 (t, J=8 Hz, 3H) ppm. HRMS (ESI+): Calcd for C20H18N3O [M+H]: 400.0135, Found: 399.2474.

Example No. 9, 10 and 11—Synthesis of Compounds Example 9, Example 10 and Example 11

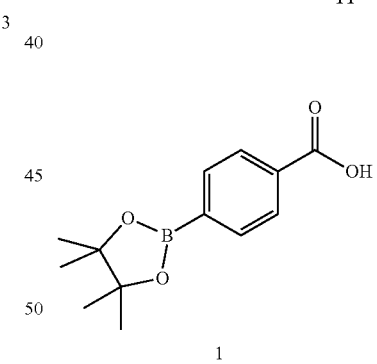

1

+

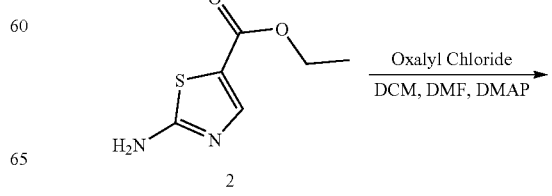

2

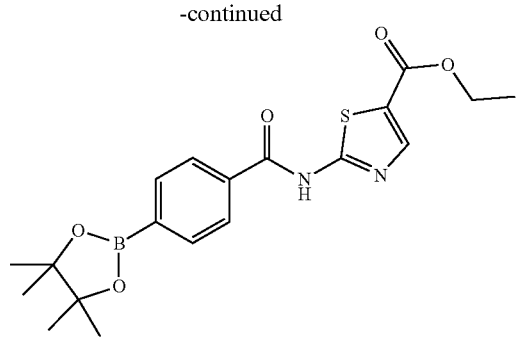
Example 9
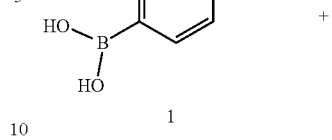
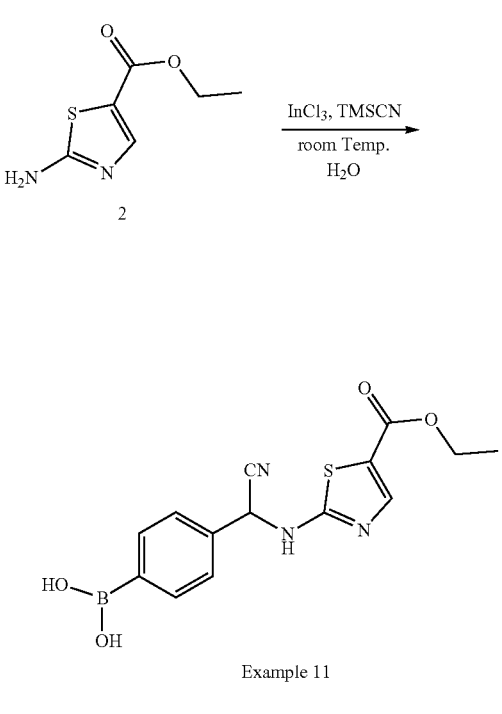
Example 11
General Procedure of Synthesis of Amide Derivative—Example 9, Example 14, Example 15, Example 16, Example 17 and Example 20
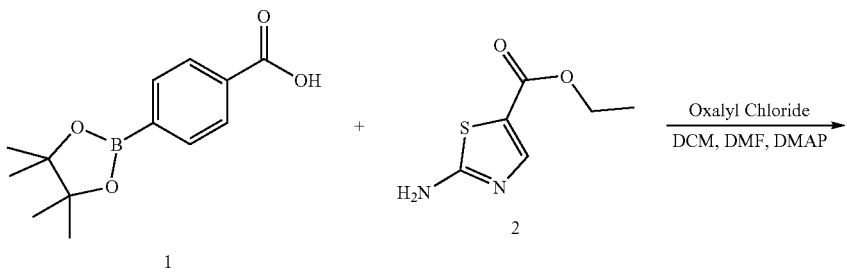

-continued
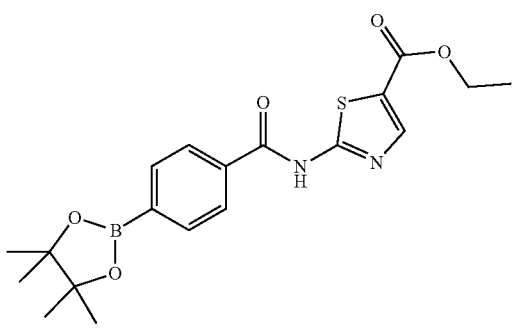
Example 9
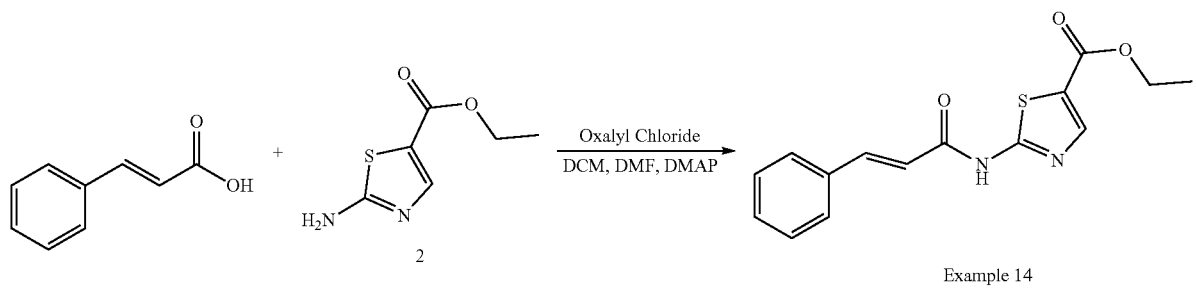 [SMILES: O=C(O)/C=C/c1ccccc1 ; CCOC(=O)c1cnc(N)s1 ; CCOC(=O)c1cnc(NC(=O)/C=C/c2ccccc2)s1]
Example 14
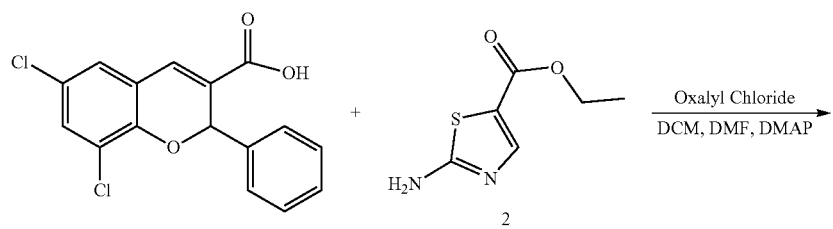
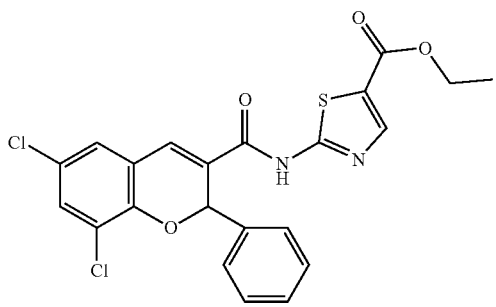
Example 15
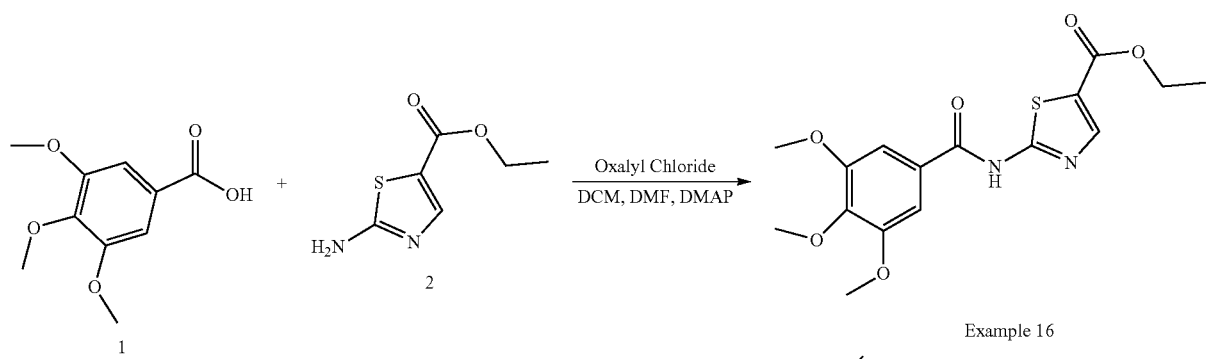
Example 16
hydrolysis

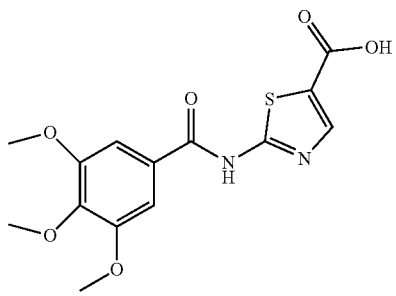
Example 19
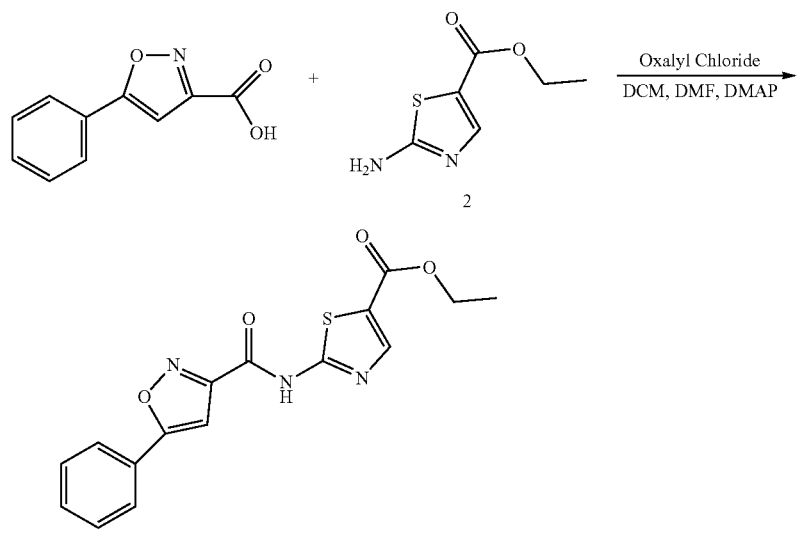
Example 17
hydrolysis
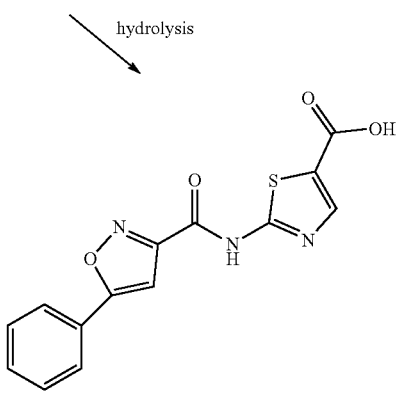
Example 18
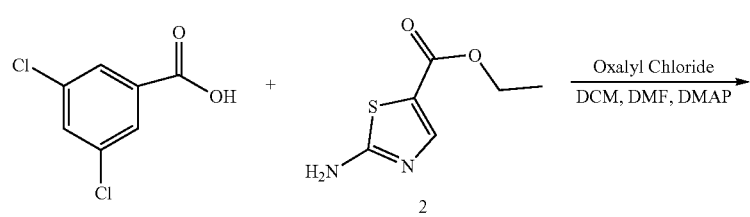

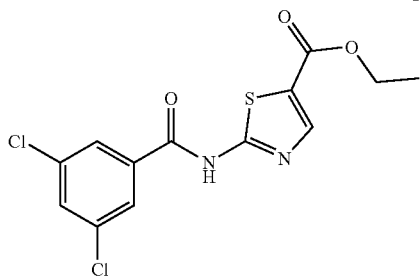

Example 20 acidic hydrolysis

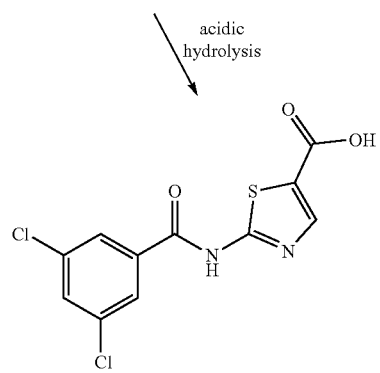

Example 21

The carboxylic acid (1.0 mmol) was dissolved in DCM (3 mL) and DMF 3 mL in a 35 mL reaction tube. To this solution was added amine (1.1 mmol) and DCC (1.2 mmol) with DMAP. The resultant reaction mixture was stirred at room temperature for 24 hrs. After completion of the reaction, the reaction was then quenched by saturated aq. NaOH solution and extracted with DCM (10×3 mL). The combined organic layers were dried over $Na_2SO_4$ and filtered. After evaporation of the organic solvent, the residue was purified by a silica gel chromatography to provide the product.

General Procedure for the Synthesis of Chromene Aminonitrile Compounds BT-339 and BT340

-continued

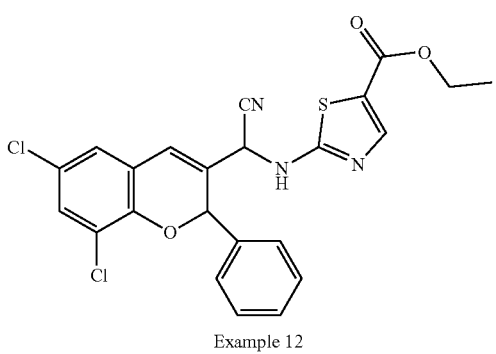

Example 12

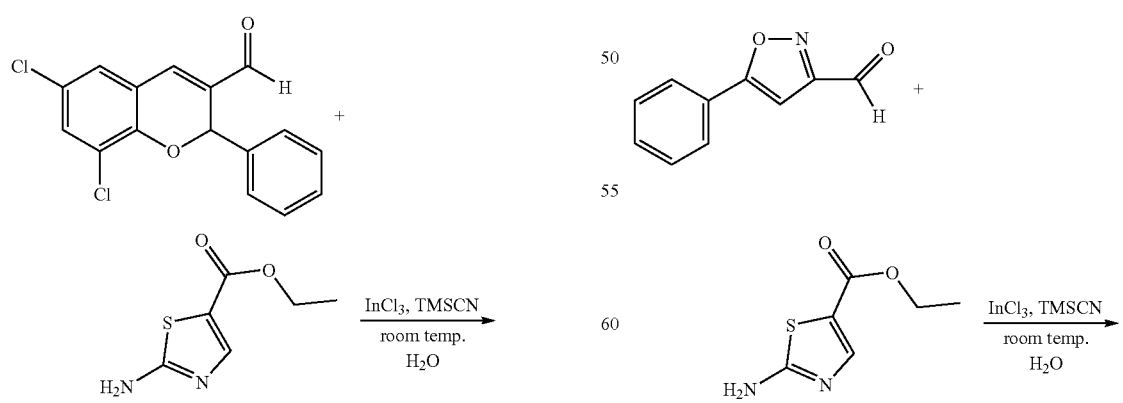

-continued

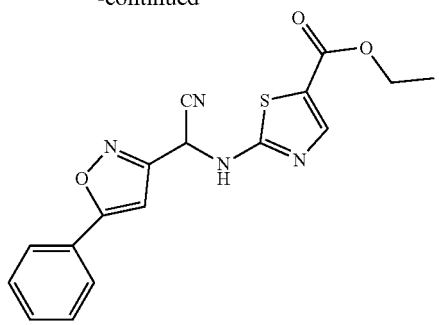

Example 13

Into a 10-mL round bottomed flask were added boronic compound aldehyde derivative (1.0 mmol), amine (1.0 mmol), TMSCN (1.2 mmol), H₂O (2 mL), and InCl₃ (0.1 mmol) sequentially. The reaction mixture was stirred vigorously at room temperature and the progress of the reaction was monitored by TLC. After stirring for 4-6 h at room temperature the solid that was formed was filtered and washed with water and hexane to yield the desired product.

Assays and Results

HCK activity inhibition efficiency for the inhibitors. Inhibiting efficiency was performed in Reaction Biology with Corp P32 radioactive kinase assay, comparing the compounds of the invention with dasatinib for HCK, Bcr-Abl and other binding kinases identified in reference. Most of the HCK inhibitors of the invention tested have $IC_{50}$ of HCK activity at about 50 uM concentrations. Examples 4, 7, 8, 12, 13, and 15 possess an $IC_{50}$ less than 50 uM; the $IC_{50}$ of Example 4 was found to be 30 uM.

Table I below describes HCK activity inhibition efficiency using compounds of the invention. HCK inhibiting efficiency was performed in Reaction Biology with Corp P32 radioactive kinase assay. Briefly, HCK kinase was delivered into the substrate solution and gently mixed, then compounds in DMSO were added into the kinase reaction mixture by Acoustic technology (Echo550; Nano liter range), and incubated for 20 minutes at room temperature. 33P-ATP was delivered into the reaction mixture to initiate the reaction. The kinase reaction was incubated for 2 hours at room temperature. Reactions were spotted onto P81 ion exchange paper, and detected kinase activity was measured by filter-binding method.

TABLE I

Enzyme Activity Summary on HCK for the inhibitors

| Example No. | % Enzyme Activity (relative to DMSO controls) | | | |
| --- | --- | --- | --- | --- |
| | HCK (50 µM) | | HCK (1 µM) | |
| 7 | 42.77 | 44.96 | 103.5 | 114.37 |
| 8 | 41.25 | 43.93 | 107.95 | 115.72 |
| 9 | 95.03 | 86.3 | 110.46 | 115.12 |
| 10 | 89.1 | 96.54 | 103.91 | 99.4 |
| 11 | 74.47 | 68.52 | 93.54 | 102.75 |
| 12 | 75.88 | 79.45 | 107.71 | 112.75 |
| 13 | 68.37 | 65.49 | 108.82 | 113 |
| 14 | 93.58 | 94.24 | 112.38 | 117.69 |
| 15 | 6.63 | 5.97 | 86.56 | 83.44 |
| 16 | 89.77 | 85.03 | 97.54 | 94.05 |
| 17 | 111.81 | 116.79 | 113.61 | 116.38 |

TABLE I-continued

Enzyme Activity Summary on HCK for the inhibitors

| Example No. | % Enzyme Activity (relative to DMSO controls) | | | |
| --- | --- | --- | --- | --- |
| | HCK (50 µM) | | HCK (1 µM) | |
| 18 | 105.88 | 113.42 | 107.38 | 94.98 |
| 19 | 94.07 | 90.7 | 99.15 | 99.98 |
| 20 | 101.04 | 97.78 | 102.49 | 110.38 |
| 21 | 76.9 | 77.73 | 96.24 | 100.43 |

HCK inhibitors reduce cell proliferation. Excessive HCK activation is associated with several types of leukemia and enhances cell proliferation and survival by physical association with oncogenic fusion proteins, and with functional interactions with receptor tyrosine kinases. Elevated HCK activity is also observed in many solid malignancies, including breast and colon cancer, and correlates with decreased patient survival rates. HCK enhances the secretion of growth factors and pro-inflammatory cytokines from myeloid cells and promotes macrophage polarization towards a wound healing and tumor-promoting alternatively activated phenotype. Inhibition of HCK activity, therefore, should inhibit cancerous cell's proliferation. Compounds of the invention were measured for inhibition of cell proliferation with CellTiter 96® AQueous One Solution Cell Proliferation Assay (MTS) from Promega in HK2 cells. The compounds of the invention were diluted to serial concentrations. HK2 cells were cultured in 10% FBS and 1% P/S. The cells were treated with the compounds of the invention for 24 hours and then 20 µl/well of CellTiter 96® AQueous One Solution Reagent was added. Values were normalized to the percentages relative to DMSO controls. Values shown are mean±SEM. Examples 8 and 15 were found to inhibit 50% of HK2 cell proliferation at 0.5 uM concentration, while Examples 7, 12, and 13 can inhibit 50% of cell proliferation at higher dose of 10 uM (FIG. 1).

LDH cytotoxicity assay for HCK inhibitors cytotoxicity. Toxicity refers to how poisonous or harmful a substance can be. In the context of pharmacology, drug toxicity occurs when a person has accumulated too much of a drug in his bloodstream, leading to adverse effects on the body. Drug toxicity may occur when the dose given is too high or the liver or kidneys are unable to remove the drug from the bloodstream, allowing it to accumulate in the body. Drug toxicity was measured with LDH cytotoxicity assay with different dosages of compounds of the invention. Only Example 12 possesses some cytotoxicity at very high dose of 50 uM, while the other inhibitors tested did not exhibit cytotoxicity even at very high dosages.

Figure 2:
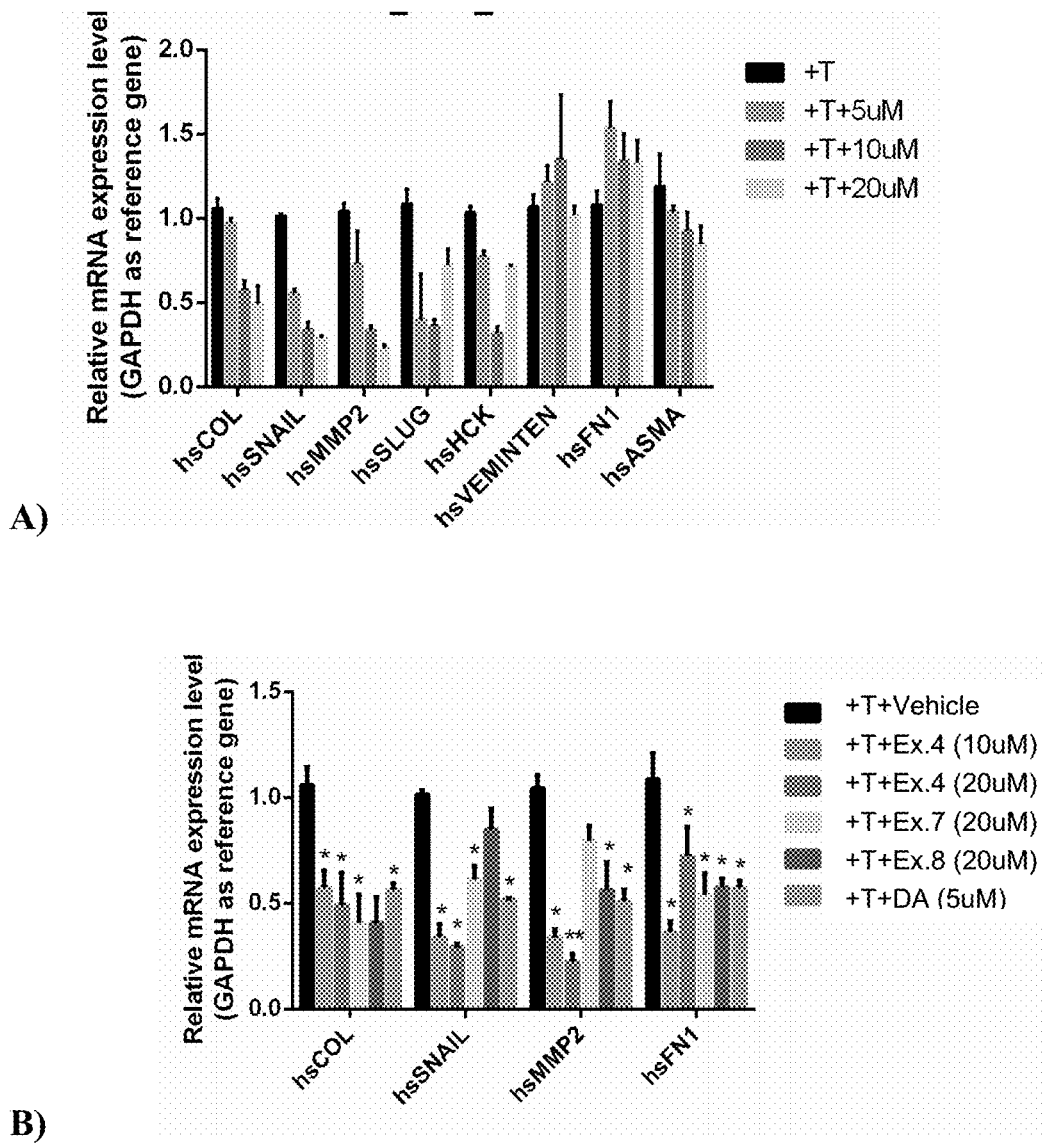
FIG. 2 demonstrates the reduction of pro-fibrosis markers mRNA levels using compounds of the invention.
Figure 3:
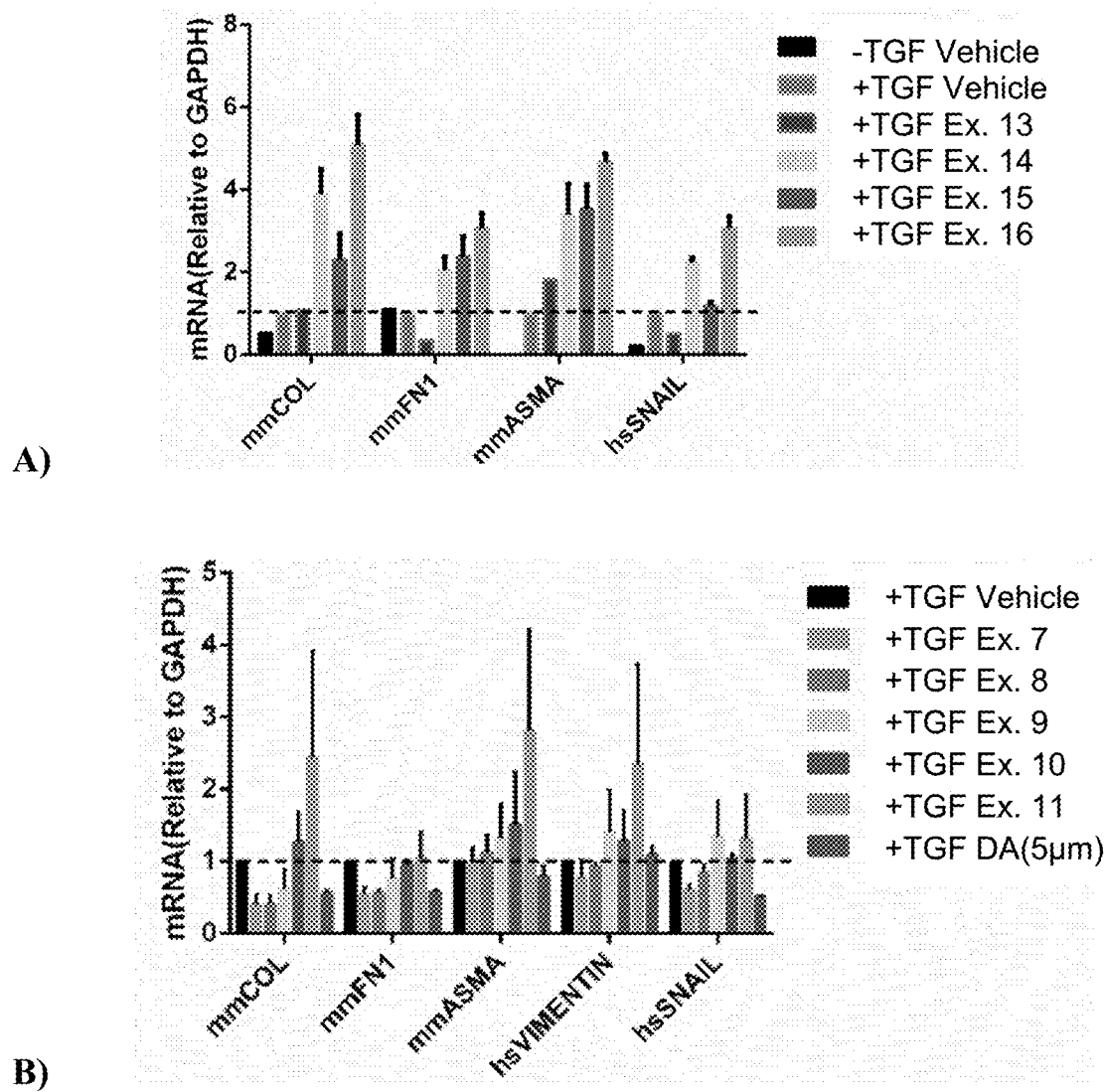
FIG. 3 demonstrates the reduction of pro-fibrosis markers mRNA levels using compounds of the invention.

Anti-fibrosis effect was investigated by fibrosis markers in mRNA level. In previous studies, HCK was found to be a key mediator of renal fibrosis through the TGF-β/Smad3 pathway. In the HK2 cells, the cells were treated with 5, 10, 20 uM of HCK inhibitor Example 4. mRNA levels of fibrosis markers collagen1, Snail, Mmp2 and Slug(Snail2) were found to be affected (FIG. 2A). The mRNA levels of Veminten, FN1 and A-Sma were not affected. HK2 cells were treated with HCK inhibitor Examples 4, 7, and 8 at 10 uM and 20 uM overnight and then stimulated with TGF-beta for 8 hours. mRNA-levels of profibrotic markers by RT-PCR (normalized to GAPDH) from mRNA isolated in the cells. Values are mean±SEM; *P=0.05, P<0.001, *P<0.001 between means; one-way ANOVA with Bonferroni multiple comparison test (FIG. 2B). Finally, it was shown that Examples 7, 8, and 13 reduced the mRNA levels of fibrosis markers (FIG. 3A and FIG. 3B).

Inhibition of HCK affects SMAD binding activity. Transforming growth factor-β(TGF-β) is the primary factor that drives fibrosis in most, if not all, forms of chronic kidney disease (CKD). TGF-β1 can induce renal fibrosis via activation of both canonical (Smad-based) and non-canonical (non-Smad-based) signalling pathways, which result in activation of myofibroblasts, excessive production of extracellular matrix (ECM) and inhibition of ECM degradation. The role of Smad proteins in the regulation of fibrosis is complex, with competing profibrotic and antifibrotic actions (including in the regulation of mesenchymal transitioning), and with complex interplay between TGF-β/Smads and other signalling pathways. Inhibition of HCK activity was found to reduce SMAD binding activity, which may explain the mechanism of HCK and HCK's inhibitor role in antifibrosis. It was found that Example 12, Example 15, and Example 8 reduce SMAD activity in HK2 cells.

In-vivo testing in a UUO model: Mice with unilateral ureteral obstruction (UUO) are treated with either an HCK inhibitor of the invention or vehicle using daily gavage starting 2 days prior to the surgery. Mice are sacrificed at either 3 or 7 days after the surgery. The inhibitory activity of the compounds of the invention as compared to controls is determined, for instance by HCK expression (such as immunohistochemistry for phosphorylated-HCK); phosphorylation of SMAD3; or the level of renal interstitial fibrosis, measured by, for instance, picrosirius red staining.

Various embodiments of the invention can be described in the text below:

[1]. A compound of formula I:

I wherein
- X is selected from O, $NR^6$, or S;
- $R^1$ is selected from O or phenyl optionally substituted with one or more substituents selected from $C_1$-$C_6$ alkyl, $C_1$-$C_6$ alkoxy, $C_1$-$C_6$ fluoroalkyl and halogen;
- $R^2$ is selected from halogen, hydrogen, $C_1$-$C_6$ alkyl, $C_1$-$C_3$ alkoxy, $C_1$-$C_3$ fluoroalkyl or phenyl;
- $R^3$ is selected from O, —OH, or —CN;
- $R^4$ is selected from —C(=O)$OR^5$, tetrazole, triazole, —CN, —C(=O)$NH_2$, —$BOR^7OR^8$, or —$BF_3^-$;
- $R^5$ is selected from hydrogen or $C_1$-$C_6$ alkyl;
- $R^6$ is selected from hydrogen or $C_1$-$C_6$ alkyl;
- $R^7$ and $R^8$ are each independently selected from hydrogen or $C_1$-$C_6$ alkyl or, together with the boron and the oxygens to which they are attached, form a 5- or 6-membered ring optionally substituted with $C_1$-$C_6$ alkyl; and
- ------ independently in each instance indicates a single bond or a double bond.

[2]. A compound of [1] above, or according to other embodiments of the invention, wherein X is O.

[3]. A compound of [1] above, or according to other embodiments of the invention, wherein X is S.

[4]. A compound of [1] above, or according to other embodiments of the invention, wherein X is $NR^6$.

[5]. A compound of [1] or [4] above, or according to other embodiments of the invention, wherein $R^6$ is hydrogen or methyl.

[6]. A compound of [1], [4] or [5] above, or according to other embodiments of the invention, wherein $R^6$ is hydrogen.

[7]. A compound of [1], [2], [3], [4], [5], or [6] above, or according to other embodiments of the invention, wherein $R^1$ is optionally substituted phenyl and ------ is a single bond.

[8]. A compound of [1], [2], [3], [4], [5], [6], or [7] above, or according to other embodiments of the invention, wherein ------ is a single bond and $R^1$ is unsubstituted phenyl.

[9]. A compound of [1], [2], [3], [4], [5], or [6] above, or according to other embodiments of the invention, wherein $R^1$ is O and ------ is a double bond.

[10]. A compound of any of [1] to [9] above, or according to other embodiments of the invention, wherein $R^2$ is halogen.

[11]. A compound of any of [1] to [10] above, or according to other embodiments of the invention, wherein $R^2$ is chloro.

[12]. A compound of any of [1] to [9] above, or according to other embodiments of the invention, wherein $R^2$ is hydrogen.

[13]. A compound of any of [1] to [12] above, or according to other embodiments of the invention, wherein $R^3$ is O and ------ is a double bond.

[14]. A compound of any of [1] to [12] above, or according to other embodiments of the invention, wherein $R^3$ is CN and ------ is a single bond.

[15]. A compound of any of [1] to [14] above, or according to other embodiments of the invention, wherein $R^4$ is —C(=O)$OR^5$.

[16]. A compound of any of [1] to [14] above, or according to other embodiments of the invention, wherein $R^5$ is selected from methyl, ethyl, i-propyl, or n-propyl.

[17]. A compound of any of [1] to [16] above, or according to other embodiments of the invention, wherein $R^5$ is ethyl.

[18]. A compound of formula II:

II wherein
- ------ independently in each instance indicates a single bond or a double bond;
- $R^{11}$ is hydrogen or $C_1$-$C_6$ alkyl;
- $R^{12}$ is hydrogen or $C_1$-$C_6$ alkyl or, when ------ is a double bond, is absent;
- $R^{13}$ is selected from hydrogen or —$CR^{14}R^{15}R^{16}$; or
- $R^{11}$ and $R^{13}$ form a 5- to 7-membered heterocyclic or heteroaryl ring, substituted with $R^{16}$;
- $R^{14}$ is hydrogen or, when ------ is a double bond, is absent;

$R^{15}$ is selected from hydrogen, cyano, $C_1$-$C_6$ haloalkyl, —C(=O)O($C_1$-$C_6$ alkyl), or —C(=O)NH$_2$, or, when $R^{11}$ and $R^{13}$ form a ring, is absent;

$R^{16}$ is a phenyl ring, optionally substituted with 1, 2, or 3 instances of $R^{17}$;

$R^{17}$ is selected independently in each instance from halogen, $C_1$-$C_6$ alkyl, $C_1$-$C_6$ alkoxy, $C_1$-$C_6$ haloalkyl, $C_1$-$C_6$ haloalkoxy, —BOR$^{18}$OR$^{19}$, —BF$_3^-$, —CN, —C(=O)NH$_2$, —C(=O)OR$^{17a}$, tetrazole, triazole, or —NO$_2$;

$R^{17a}$ is selected from hydrogen or $C_1$-$C_6$ alkyl;

$R^{18}$ and $R^{19}$ are each independently selected from hydrogen or $C_1$-$C_6$ alkyl or, together with the boron and the oxygens to which they are attached, form a 5- or 6-membered ring optionally substituted with $C_1$-$C_6$ alkyl; and $R^{20}$ is selected from hydrogen, $C_1$-$C_6$ alkyl, a 5- or 6-membered heteroaryl optionally substituted with $C_1$-$C_6$ alkyl, or phenyl optionally substituted independently in each instance with one or more of halogen, $C_1$-$C_6$ alkyl, $C_1$-$C_3$ alkoxy, $C_1$-$C_3$ haloalkoxy, $C_1$-$C_3$ haloalkyl, a heterocycle, —CN, and —C(=O)NH$_2$

[19]. A compound of [18] above, or according to other embodiments of the invention, wherein $R^{11}$ and $R^{13}$ form a 5- to 7-membered heterocyclic or heteroaryl ring, substituted with $R^{16}$.

[20]. A compound [18] or [19] above, or according to other embodiments of the invention, wherein said compound is of formula:

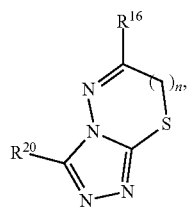

wherein n is 0, 1, or 2.

[21]. A compound of [20] above, or according to other embodiments of the invention, wherein n is 0 or 1.

[22]. A compound of any of [18] to [21] above, or according to other embodiments of the invention, wherein each instance of $R^{17}$ is selected independently from bromine, fluorine, chlorine, methyl, methoxy, —CF$_3$, —OCF$_3$, —BF$_3$, or

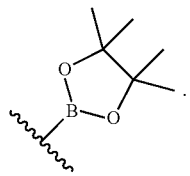 [SMILES: *B1OC(C)(C)C(C)(C)O1]

[23]. A compound of any of [18] to [22] above, or according to other embodiments of the invention, wherein one $R^{17}$ is in the para position.

[24]. A compound of any of [18] to [23] above, or according to other embodiments of the invention, wherein said compound is of formula:

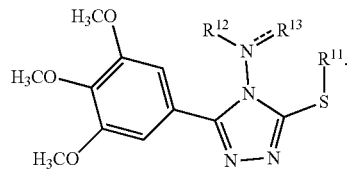

[25]. A compound of any of [18], [19], or [24] above, or according to other embodiments of the invention, wherein $R^{11}$ is hydrogen.

[26]. A compound of any of [18], [19], [22], [23], [24], or [25] above, or according to other embodiments of the invention, wherein $R^{12}$ is hydrogen.

[27]. A compound of any of [18], [19], or [22] to [26] above, or according to other embodiments of the invention, wherein $R^{13}$ is hydrogen.

[28]. A compound of any of [18], [19], or [22] to [26] above, or according to other embodiments of the invention, wherein $R^{13}$ is —CR$^{14}$R$^{15}$R$^{16}$.

[29]. A compound of any of [18], [19], or [22] to [28] above, or according to other embodiments of the invention, wherein ====== is a single bond.

[30]. A compound of any of 18], [19], or [22] to [28] above, or according to other embodiments of the invention, wherein ====== is a double bond and $R^{15}$ is hydrogen.

[31]. A compound of formula III:

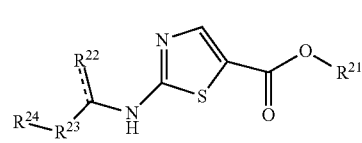

wherein $R^{21}$ is hydrogen or $C_1$-$C_6$ alkyl;

------ independently in each instance indicates a single bond or a double bond;

$R^{22}$ is cyano when ====== is a single bond, or is selected from =O or =N—OH when ====== is a double bond;

$R^{23}$ is absent or is selected from —CH=CH— or a 5- or 6-membered heteroaryl;

$R^{24}$ is a phenyl ring, optionally substituted with 1, 2, or 3 instances of $R^{25}$;

$R^{25}$ is selected independently in each instance from halogen, $C_1$-$C_6$ alkyl, $C_1$-$C_6$ alkoxy, $C_1$-$C_6$ haloalkyl, $C_1$-$C_6$ haloalkoxy, —BOR$^{26}$OR$^{27}$, —BF$_3^-$, —CN, —C(=O)NH$_2$, —C(=O)OR$^{27a}$, tetrazole, triazole, —NO$_2$, guanidine, and an amidoxime;

$R^{26}$ and $R^{27}$ are each selected from hydrogen or $C_1$-$C_6$ alkyl or, together with the boron and the oxygens to which they are attached, form a 5- or 6-membered ring optionally substituted with one or more $C_1$-$C_6$ alkyl groups; and $R^{27a}$ is selected from hydrogen or $C_1$-$C_6$ alkyl.

[32]. A compound of [31] above, or according to other embodiments of the invention, wherein $R^{23}$ is absent, and the compound is of formula:

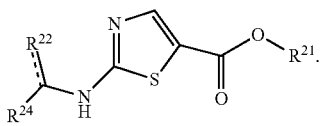

[33]. A compound of [31] above, or according to other embodiments of the invention, wherein $R^{23}$ is —CH=CH—, and the compound is of formula:

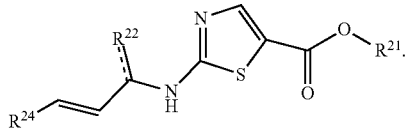

[34]. A compound of [31] above, or according to other embodiments of the invention, wherein $R^{23}$ is a 5- or 6-membered heteroaryl.

[35]. A compound of [31] or [34] above, or according to other embodiments of the invention, wherein $R^{23}$ is selected from isoxazole and oxazole.

[36]. A compound of any of [31], [34] or [35] above, or according to other embodiments of the invention, wherein $R^{23}$ is isoxazole, and the compound is of formula:

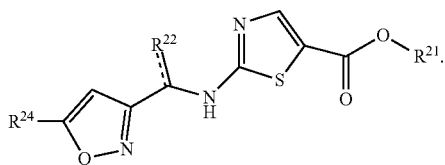

[37]. A compound of any of [31] to [36] above, or according to other embodiments of the invention, wherein $R^{21}$ is selected from hydrogen, methyl, or ethyl.

[38]. A compound of any of [31] to [37] above, or according to other embodiments of the invention, wherein ----- is a double bond and $R^{22}$ is O, forming =O.

[39]. A compound of any of [31] to [37] above, or according to other embodiments of the invention, wherein ----- is a single bond and $R^{22}$ is cyano, forming —CN.

[40]. A compound of any of [31] to [39] above, or according to other embodiments of the invention, wherein $R^{24}$ is unsubstituted phenyl.

[41]. A compound of any of [31] to [39] above, or according to other embodiments of the invention, wherein $R^{24}$ is

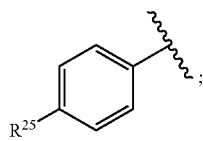

and
$R^{25}$ is —$BOR^{26}OR^{27}$.

[42]. A compound of any of [31] to [39] or [41] above, or according to other embodiments of the invention, wherein $R^{25}$ is selected from —$B(OH)_2$ or

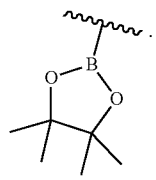

[43]. A compound of any of [31] to [39] above, or according to other embodiments of the invention, wherein $R^{24}$ is selected from

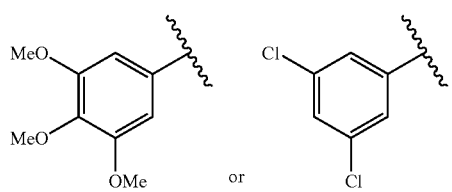

[44]. A pharmaceutical composition comprising a pharmaceutically acceptable carrier and a compound of any one of [1] to [43] above, or according to other embodiments of the invention.

[45]. A method for treating fibrosis or a fibrotic disease in a patient, the method comprising administering to a patient an effective amount of a compound according to any one of [1] to [43] above, or an effective amount of a pharmaceutical composition of [44], or according to other embodiments of the invention.

[46]. The method of [45] above, or according to other embodiments of the invention, wherein the fibrosis or fibrotic disease is selected from renal fibrosis, pulmonary fibrosis, cystic fibrosis, cirrhosis, fibrosis of the heart, mediastinal fibrosis, retroperitoneal cavity fibrosis, bone marrow fibrosis, hypertrophic scars, keloids, scleroderma, systemic sclerosis, Crohn's disease, Peyronie's disease, lupus nephritis, folic acid nephropathy, and fibrosis induced by radiation, infection, chemotherapeutic drugs, surgery, burns or inhalation.

[47]. A method for treating a chronic kidney disease, renal fibrosis, or chronic renal allograft injury in a patient, the method comprising administering to a patient an effective amount of a compound according to any one of [1] to [43] above, or an effective amount of a pharmaceutical composition of [44], or according to other embodiments of the invention.

[48]. A method for treating a disease or disorder in a patient chosen from solid malignancy and hematological malignancy, the method comprising administering to a patient an effective amount of a compound according to any one of [1] to [43] above, or an effective amount of a pharmaceutical composition of [44], or according to other embodiments of the invention.

[49]. The method of [48] above, or according to other embodiments of the invention, wherein the disease or disorder is breast cancer, colon cancer, rectal cancer, or stomach cancer.

[50]. The method of [48] above, or according to other embodiments of the invention, wherein the disease or disorder is chronic myeloid leukemia, acute lymphoblastic leukemia, a myelodysplastic syndrome, multiple myeloma or a lymphoma.

[51]. A method for treating a disease or disorder in a patient chosen from an autoimmune or inflammatory disease, the method comprising administering to a patient an effective amount of a compound according to any one of [1] to [43] above, or an effective amount of a pharmaceutical composition of [44], or according to other embodiments of the invention.

[52]. The method of [51] above, or according to other embodiments of the invention, wherein the disease or disorder is rheumatoid arthritis or chronic obstructive pulmonary disease.

[53]. A method for treating a disease or disorder in a patient where the disease or disorder involves the dysregulation of hematopoietic cell kinase (HCK) signaling, the method comprising administering to a patient an effective amount of a compound according to any one of [1] to [43] above, or an effective amount of a pharmaceutical composition of [44], or according to other embodiments of the invention.

[54]. A method for inhibiting hematopoietic cell kinase (HCK) activation, said method comprising bringing hematopoietic cell kinase (HCK) into contact with a compound according to any one of [1] to [43] above, or a pharmaceutical composition of [44], or according to other embodiments of the invention.

[55]. The method of [54] above, or according to other embodiments of the invention, wherein the method is an in vitro method.

[56]. The method of [54] above, or according to other embodiments of the invention, wherein the method is an in vivo method.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention. While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

We claim:

1. A compound of formula I:

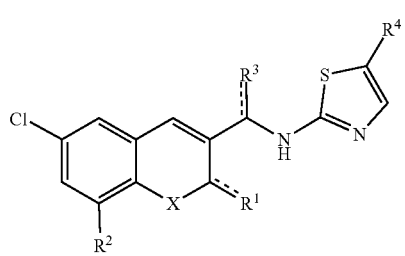

wherein
X is selected from O, $NR^6$, or S;
$R^1$ is selected from O or phenyl optionally substituted with one or more substituents selected from $C_1$-$C_6$ alkyl, $C_1$-$C_6$ alkoxy, $C_1$-$C_6$ fluoroalkyl and halogen;
$R^2$ is selected from halogen, hydrogen, $C_1$-$C_6$ alkyl, $C_1$-$C_3$ alkoxy, $C_1$-$C_3$ fluoroalkyl or phenyl;
$R^3$ is selected from O, —OH, or —CN;
$R^4$ is selected from —C(=O)$OR^5$, tetrazole, triazole, —CN, —C(=O) $NH_2$, —$BOR^7OR^8$, or —$BF_3^-$;
$R^5$ is selected from hydrogen or $C_1$-$C_6$ alkyl;
$R^6$ is selected from hydrogen or $C_1$-$C_6$ alkyl;
$R^7$ and $R^8$ are each independently selected from hydrogen or $C_1$-$C_6$ alkyl or, together with the boron and the oxygens to which they are attached, form a 5- or 6-membered ring optionally substituted with $C_1$-$C_6$ alkyl; and
----- independently in each instance indicates a single bond or a double bond.

2. A compound according to claim 1, wherein X is O.
3. A compound according to claim 1, wherein X is $NR^6$.
4. A compound according to claim 1, wherein $R^4$ is-C(=O) $OR^5$.
5. A compound according to claim 1, wherein:
X is O or NH;
$R^1$ is selected from optionally substituted phenyl or O;
$R^2$ is selected from hydrogen or chloro;
$R^3$ is selected from O or CN;
$R^4$ is-C(=O) $OR^5$;
$R^5$ is ethyl; and
----- independently in each instance indicates a single bond or a double bond.

6. A compound according to claim 1, wherein said compound is selected from:

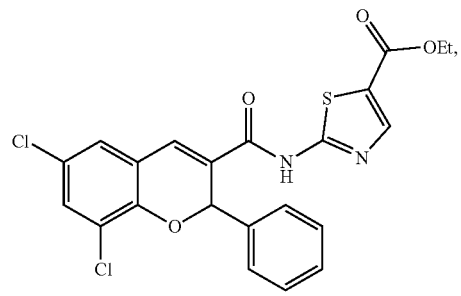

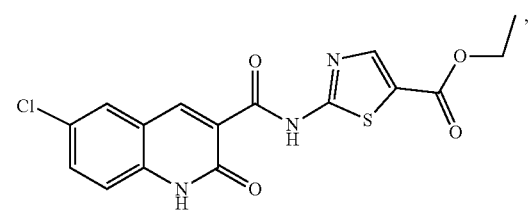

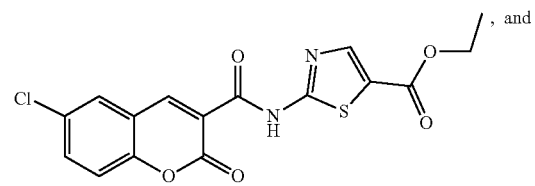

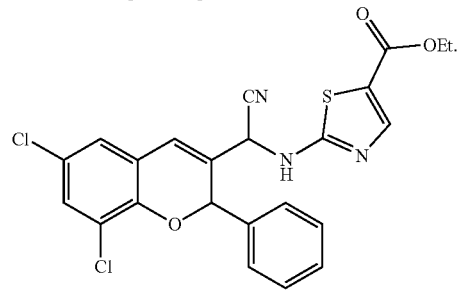

7. A pharmaceutical composition comprising a compound according to claim 1 and a pharmaceutically acceptable carrier, adjuvant, or vehicle.

8. A method for treating a disease or disorder in a patient, comprising administering to said patient an effective amount of a compound according to claim 1, wherein said disease or disorder is selected from fibrosis or a fibrotic disease; a chronic kidney disease, renal fibrosis, or chronic renal allograft injury; solid malignancy or hematological malignancy; an autoimmune or inflammatory disease; or wherein the disease or disorder involves the dysregulation of hematopoietic cell kinase (HCK) signaling.

9. A method for inhibiting hematopoietic cell kinase (HCK) activation, said method comprising bringing hematopoietic cell kinase (HCK) into contact with a compound according to claim 1.

10. A compound according to claim 3, wherein $R^6$ is selected from hydrogen or methyl.

11. A compound according to claim 1, wherein $R^6$ is hydrogen.

12. A compound according to claim 6, wherein $R^1$ is unsubstituted phenyl and ----- is a single bond.

13. A compound according to claim 1, wherein $R^1$ is O and ----- is a double bond.

14. A compound according to claim 1, wherein $R^2$ is halogen.

15. A compound according to claim 1, wherein $R^2$ is chloro.

16. A compound according to claim 1, wherein $R^2$ is hydrogen.

17. A compound according to claim 1, wherein $R^3$ is O and ----- is a double bond.

18. A compound according to claim 1, wherein $R^3$ is CN and ----- is a single bond.

19. A method for treating a disease or disorder in a patient, comprising administering to said patient an effective amount of a compound according to claim 6, wherein said disease or disorder is selected from fibrosis or a fibrotic disease; a chronic kidney disease, renal fibrosis, or chronic renal allograft injury; solid malignancy or hematological malignancy; an autoimmune or inflammatory disease; or wherein the disease or disorder involves the dysregulation of hematopoietic cell kinase (HCK) signaling.

20. A method for inhibiting hematopoietic cell kinase (HCK) activation, said method comprising bringing hematopoietic cell kinase (HCK) into contact with a compound according to claim 6.

* * * * *

UNITED STATES PATENT AND TRADEMARK OFFICE
CERTIFICATE OF CORRECTION

Page 1 of 1

PATENT NO. : 12,378,235 B2
APPLICATION NO. : 17/593960
DATED : August 5, 2025
INVENTOR(S) : Murphy et al.

It is certified that error appears in the above-identified patent and that said Letters Patent is hereby corrected as shown below:

In the Claims

Column 65, Line 22: Claim 12, Delete "claim 6" and insert -- claim 1 --

Signed and Sealed this
Seventh Day of October, 2025

John A. Squires
*Director of the United States Patent and Trademark Office*